(12) United States Patent
Kato et al.

(10) Patent No.: US 8,304,536 B2
(45) Date of Patent: Nov. 6, 2012

(54) PHTHALOCYANINE COMPOUND

(75) Inventors: Taku Kato, Funabashi (JP); Naoki Otani, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 136 days.

(21) Appl. No.: 12/675,543

(22) PCT Filed: Aug. 26, 2008

(86) PCT No.: PCT/JP2008/065149
§ 371 (c)(1),
(2), (4) Date: Feb. 26, 2010

(87) PCT Pub. No.: WO2009/028478
PCT Pub. Date: Mar. 5, 2009

(65) Prior Publication Data
US 2010/0228021 A1    Sep. 9, 2010

(30) Foreign Application Priority Data

Aug. 28, 2007  (JP) ................................. 2007-220463

(51) Int. Cl.
*C07D 487/22* (2006.01)
*C07B 47/00* (2006.01)

(52) U.S. Cl. ....................................................... 540/145

(58) Field of Classification Search ................... 540/145
See application file for complete search history.

(56) References Cited

U.S. PATENT DOCUMENTS

| 4,606,859 | A | 8/1986 | Duggan et al. |
| 5,137,798 | A | 8/1992 | Duggan et al. |
| 5,594,128 | A | 1/1997 | Wolleb |
| 5,641,879 | A | 6/1997 | Wolleb et al. |
| 2006/0000388 | A1 | 1/2006 | Campbell et al. |

FOREIGN PATENT DOCUMENTS

| JP | 60-209583 A | 10/1985 |
| JP | 61-154888 A | 7/1986 |
| JP | 62-102569 A | 5/1987 |
| JP | 6-293186 A | 10/1994 |
| JP | 8-209009 A | 8/1996 |
| JP | 2002-83979 A | 3/2002 |
| JP | 2003-211847 A | 7/2003 |
| JP | 2003-321630 A | 11/2003 |
| JP | 2004-342693 A | 12/2004 |
| JP | 2004-349657 A | 12/2004 |
| JP | 2005-236278 A | 9/2005 |
| JP | 2005-537319 A | 12/2005 |
| WO | WO-2007/000781 A1 | 1/2007 |
| WO | WO-2007/002981 A1 | 1/2007 |

OTHER PUBLICATIONS von Gottfried Markl et al., "Tetrakis(diethyl-phosphonat)-, Tetrakis(ethyl-phenylphosphinat)-und Tetrakis(diphenylphosphinoxid)- substituierte Phthalocyanine", Helvetica Chimica Acta, vol. 87, pp. 825-844, Apr. 29, 2004.

Wesley M. Sharman et al., "Novel Water-Soluble Phthalocyanines Substituted with Phosphonate Moieties on the Benzo Rings", Tetrahedron Letters, vol. 37, No. 33, pp. 5831-5834, 1996.
Paul M. Burnham et al., "Structural characterisation of a red phthalocyanine", Chemical Communications, United Kingdom, pp. 2064-2065 (2003).
Robert D. George et al., "Synthesis of 3-Nitrophthalonitrile and Tetra-α-substituted Phthalocyanines", Journal of Heterocyclic Chemistry, pp. 495-498, Mar.-Apr. 1995.
Dieter Wohrle et al., "A Simple Synthesis of 4,5-Disubstituted 1,2-Dicyanobenzenes and 2,3,9,10,16,17,23,24-Octasubstituted Phthalocyanines", Synthesis, pp. 194-196, Feb. 1993.
Shikizai Kiyokaishi, Journal of Japan Society of Color Material Japan, vol. 75, No. 5, pp. 214-220, May 2002.

*Primary Examiner* — Paul V. Ward
(74) *Attorney, Agent, or Firm* — Birch, Stewart, Kolasch & Birch, LLP

(57) ABSTRACT

Disclosed is a phthalocyanine compound characterized by being represented by the formula (1) below. This phthalocyanine compound has good affinity to titania, and is suitably used for an organic thin film of an organic solar cell and the like.

(1)

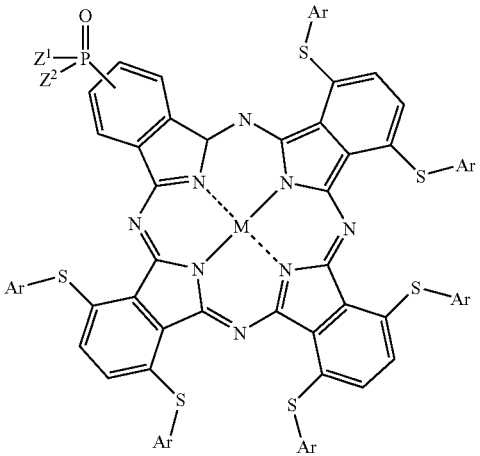

[In the formula, M represents a hydrogen atom or a central metal; $Z^1$ and $Z^2$ independently represent a hydroxy group, an alkoxy group having 1 to 18 carbon atoms or a phenyl group; and Ar represents at least one aryl group selected from those represented by the following formulae (2) to (12).

(2)

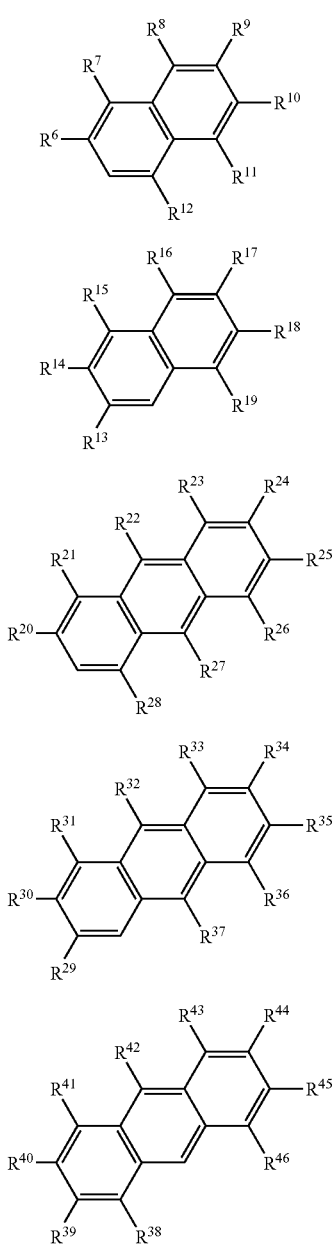
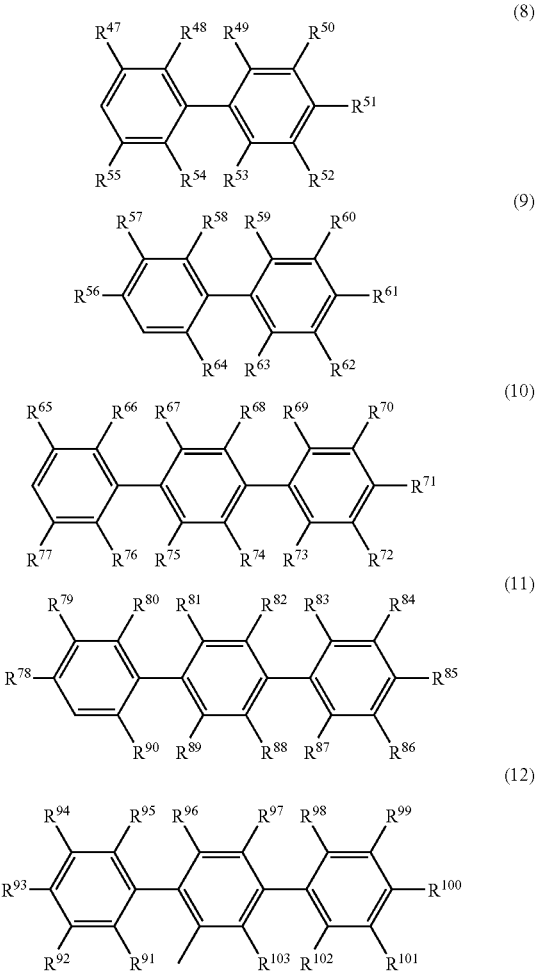

(In the formulae (2) to (12), $R^1$ to $R^{103}$ independently represent a hydrogen atom, a halogen atom, a hydroxy group, an amino group, a silanol group, a thiol group, a carboxyl group, a phosphoric acid group, a phosphate group, an ester group, a thioester group, an amide group, a nitro group, a monovalent hydrocarbon group, an organoxy group, an organoamino group, an organosilyl group, an organothio group, an acyl group or a sulfone group.)]

13 Claims, 1 Drawing Sheet

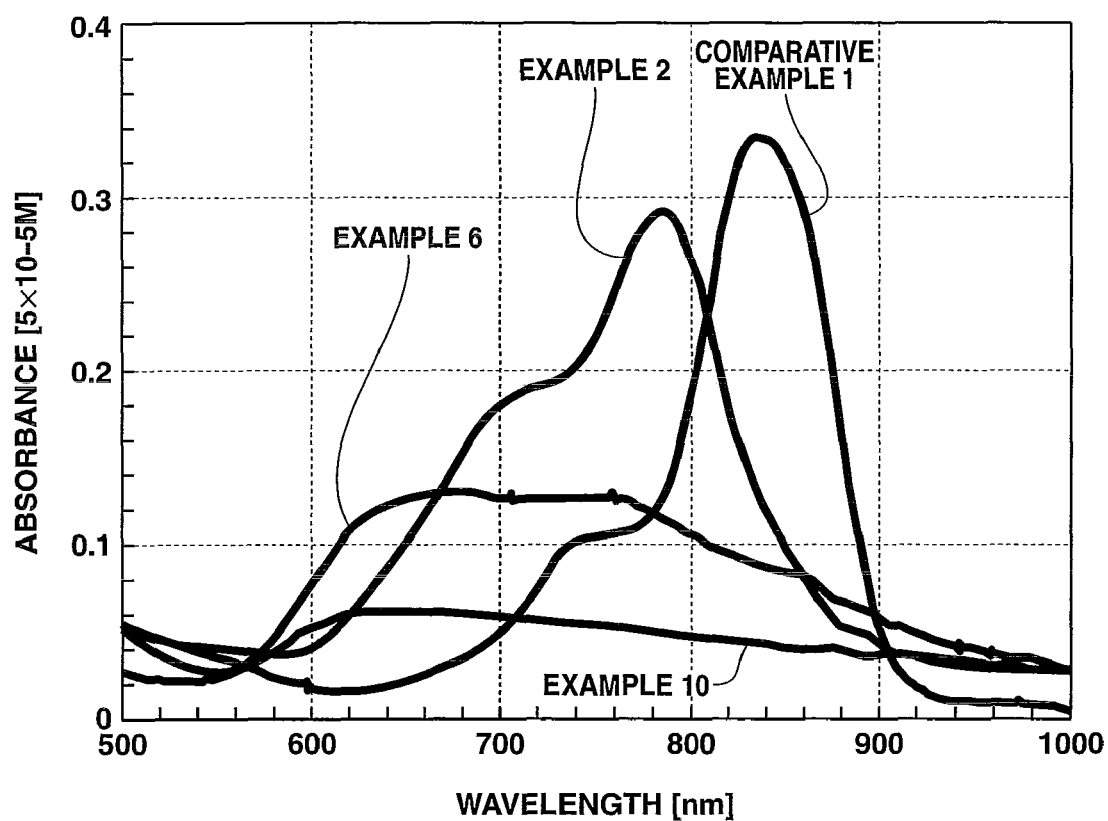

PHTHALOCYANINE COMPOUND

TECHNICAL FIELD

This invention relates to a phthalocyanine compound and more particularly, to a phthalocyanine compound having both a phosphoric ester group and a thioaryl group.

BACKGROUND ART

In recent years, consideration has been given to global environmental problems such as of global warming phenomena, for which there have been expected practical applications of solar cells that are a clean energy source wherein no petroleum recourse is burnt.

Of such cells, organic solar cells have been being studied and developed because their ease in providing a large-sized area and low costs are expected (Patent Document 1: JP-A 2004-342693, and Patent Document 2: JP-A 2004-349657). A variety of organic solar cell structures have been now proposed, and the trend of the studies and developments is to improve a photoelectric conversion efficiency, to improve charge separability, and to secure the stability of electronic device.

One of electrode materials of organic solar cells includes titania (titanium dioxide), and it is known that this material functions as an n-type semiconductor and is useful as one member of bulk heterojunction devices (Patent Document 3: JP-A 2005-236278).

An existing organic film in conjunction with this titania is only built up on the titania and is poor in interfacial adhesion with titania, with the attendant problem that the photoelectric conversion efficiency is not improved.

However, no molecular design of organic compound has never been made for the purpose of improving adhesion between titania and the organic film.

By the way, phthalocyanine compounds are long known as a dye or pigment that assumes a blue to green color.

Phthalocyanine compounds used as a functional dye have been employed in a diversity of fields, and an instance used as one of members of organic solar cells has been reported (Patent Document 4: JP-A 2002-83979).

However, this compound has never been subjected, up to now, to molecular design of improving affinity for and adhesion with titania as set out above.
Patent Document 1: JP-A 2004-342693
Patent Document 2: JP-A 2004-349657
Patent Document 3: JP-A 2005-236278
Patent Document 5: JP-A 2002-83979

DISCLOSURE OF THE INVENTION

Problems to be Solved by the Invention

The invention has been made under such circumstances as set forth above and has for its object the provision of a phthalocyanine compound that has good affinity for titania and can be conveniently utilized as an organic thin film such as of organic solar cells.

Means for Solving the Problem

In order to improve interfacial adhesion between an organic film and titania, the present applicant has hitherto made use of metal phthalocyanine (hereinafter abbreviated as MtPC) derivatives as an organic material to make studies on synthesis of MtPC having a functional group, which has affinity for titania, at a side chain.

In order to allow functional development of MtPC derivatives as an organic solar cell, it is necessary for them (1) to have affinity for titania serving as an electrode and ensure good adhesion with titania when formed as an organic film, (2) to have an absorption maximum wavelength that is in the vicinity of or in a near-infrared region, and (3) to exhibit high solubility in organic solvents and be capable of forming a uniform thin film according many wet processes.

The present inventors have made intensive studies on the molecular design of MtPC that enables functional development as an organic solar cell and, as a result, found that a MtPC derivative of a novel type wherein a phosphoric ester group and a thioaryl group are introduced into a MtPC molecule has good affinity for titania, has an absorption maximum wavelength that is in the vicinity of or in a near-infrared region and exhibits high solubility in organic solvents, thereby arriving at completion of the invention.

More particularly, the invention provides:
1. A phthalocyanine compound, characterized by being represented by the formula (1)

[Chemical Formula 1]

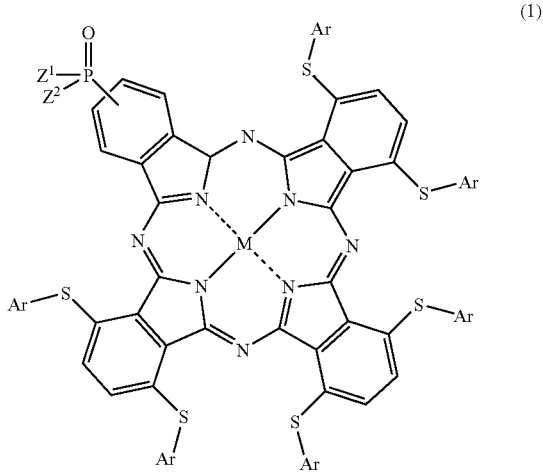

[wherein M represents a hydrogen atom, or a central metal selected from Li, Be, Na, Mg, Al, Si, K, Ca, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Ba, Hf, Ta, W, Re, Os, Ir, Pt, Au, Hg, Tl, Pb, Ce, Pr, Nd, Pm, Sm, Eu, Gd, Tb, Dy, Ho, Er, Tm, Yb, Lu, Th, Pa, U, Np and Am, $Z^1$ and $Z^2$ independently represent a hydroxyl group, an alkoxy group having 1 to 18 carbon atoms, or a phenyl group, and Ar represents at least one aryl group selected from the formulas (2) to (12)

[Chemical Formula 2]

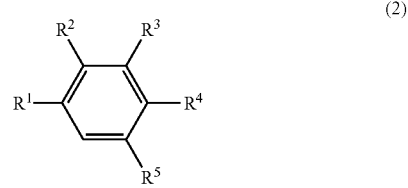

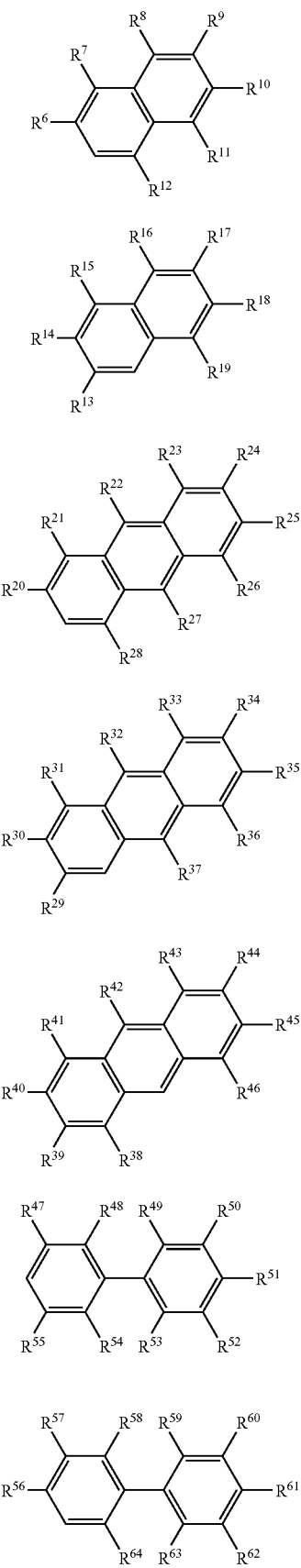

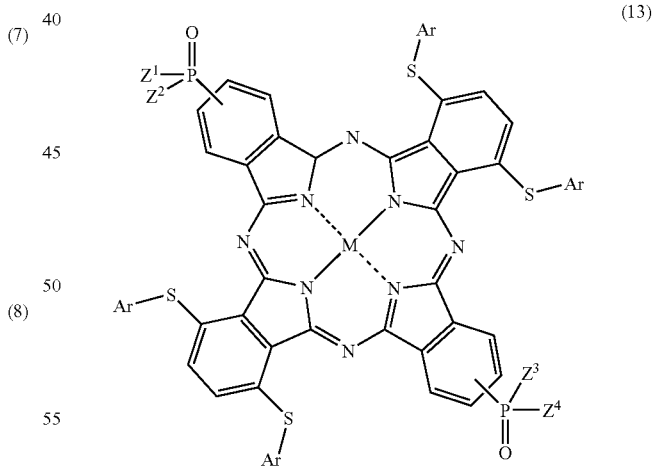

(in the formulas (2) to (12), $R^1$ to $R^{103}$ independently represent a hydrogen atom, a halogen atom, a hydroxyl group, an amino group, a silanol group, a thiol group, a carboxyl group, a phosphoric group, a phosphoric ester group, an ester group, a thioester group, an amide group, a nitro group, a monovalent hydrocarbon group, an organooxy group, an organoamino group, an organosilyl group, an organothio group, an acyl group or a sulfone group)];

2. A phthalocyanine compound, characterized by being represented by the formula (13)

[Chemical Formula 3]

[wherein M represents a hydrogen atom, or a central metal selected from Li, Be, Na, Mg, Al, Si, K, Ca, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Ba, Hf, Ta, W, Re, Os, Ir, Pt, Au, Hg, Tl, Pb, Ce, Pr, Nd, Pm, Sm, Eu, Gd, Tb, Dy, Ho, Er, Tm, Yb, Lu, Th, Pa, U, Np and Am, $Z^1$ to $Z^4$ independently represent a hydroxyl group, an alkoxy group having 1 to 18 carbon atoms, or a phenyl group, and Ar represents at least one aryl group selected from the formulas (2) to (12)

[Chemical Formula 4]

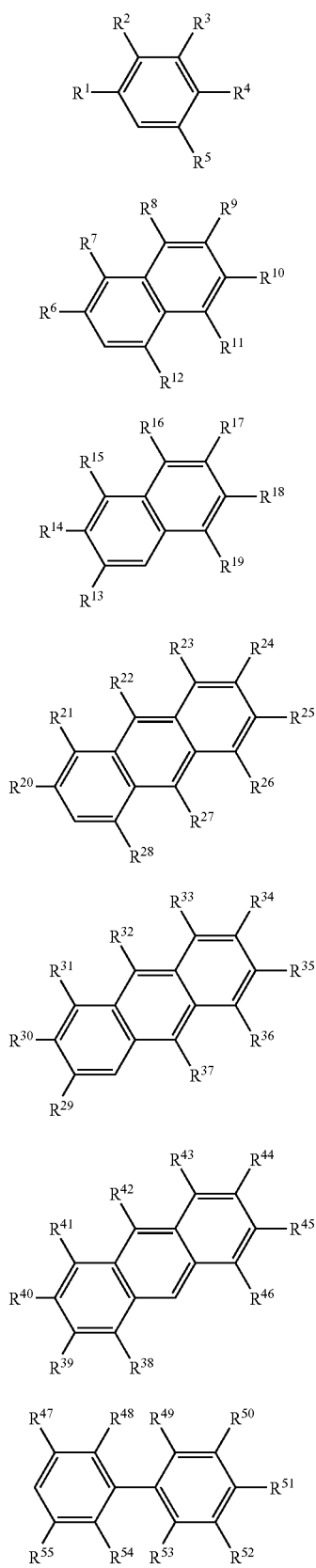

(2) 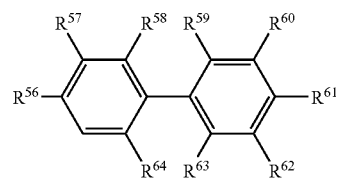

(3) 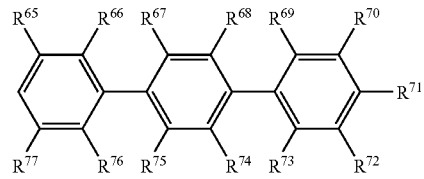

(4) 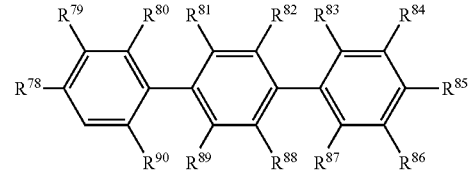

(5) 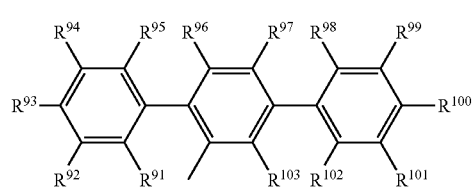

(6)

(7)

(8)

(in the formulas (2) to (12), $R^1$ to $R^{103}$ independently represent a hydrogen atom, a halogen atom, a hydroxyl group, an amino group, a silanol group, a thiol group, a carboxyl group, a phosphoric group, a phosphoric ester group, an ester group, a thioester group, an amide group, a nitro group, a monovalent hydrocarbon group, an organooxy group, an organoamino group, an organosilyl group, an organothio group, an acyl group or a sulfone group)];

3. A phthalocyanine compound, characterized by being represented by the formula (14)

[Chemical Formula 5]

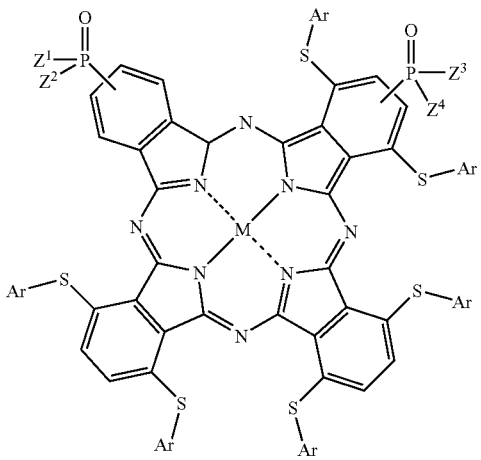

(14)

[wherein M represents a hydrogen atom, or a central metal selected from Li, Be, Na, Mg, Al, Si, K, Ca, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Ba, Hf, Ta, W, Re, Os, Ir, Pt, Au, Hg, Tl, Pb, Ce, Pr, Nd, Pm, Sm, Eu, Gd, Tb, Dy, Ho, Er, Tm, Yb, Lu, Th, Pa, U, Np and Am, $Z^1$ to $Z^4$ independently represent a hydroxyl group, an alkoxy group having 1 to 18 carbon atoms, or a phenyl group, and Ar represents at least one aryl group selected from the formulas (2) to (12)

[Chemical Formula 6]

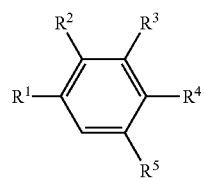
(2)

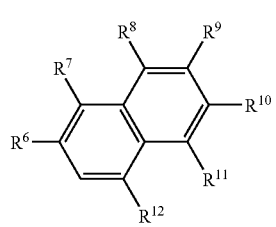
(3)

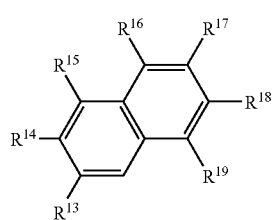
(4)

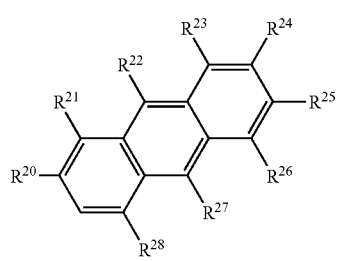
(5)

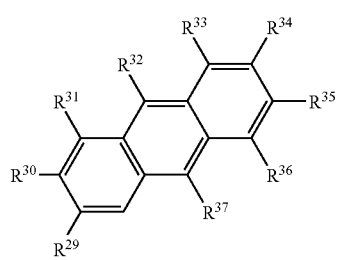
(6)

-continued

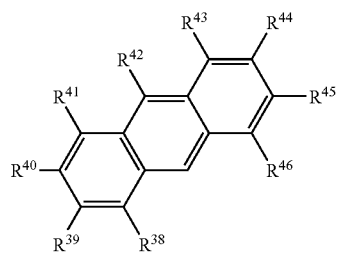
(7)

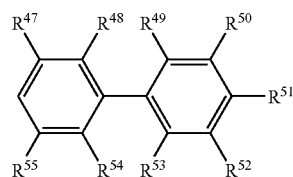
(8)

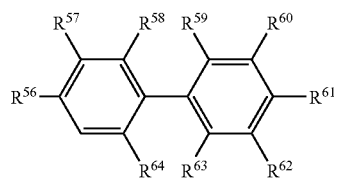
(9)

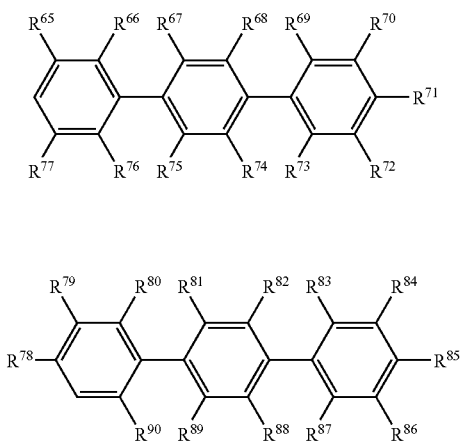
(10)

(11)

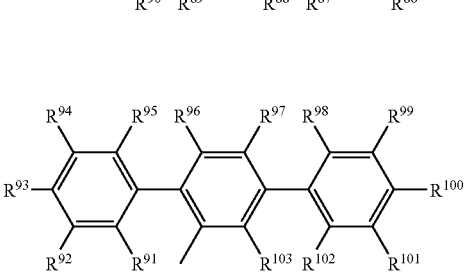
(12)

(in the formulas (2) to (12), $R^1$ to $R^{103}$ independently represent a hydrogen atom, a halogen atom, a hydroxyl group, an amino group, a silanol group, a thiol group, a carboxyl group, a phosphoric group, a phosphoric ester group, an ester group, a thioester group, an amide group, a nitro group, a monovalent hydrocarbon group, an organooxy group, an organoamino group, an organosilyl group, an organothio group, an acyl group or a sulfone group)];

4. A phthalocyanine compound, characterized by being represented by the formula (15)

[Chemical Formula 7]

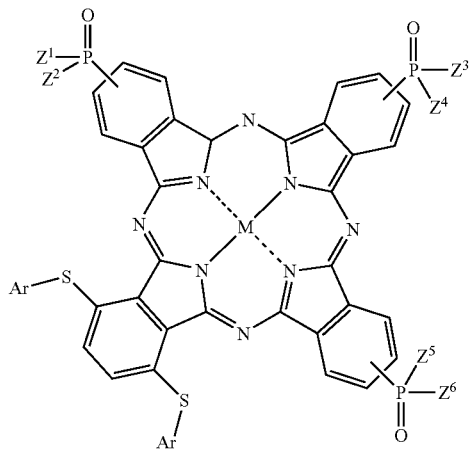
(15)

[wherein M represents a hydrogen atom, or a central metal selected from Li, Be, Na, Mg, Al, Si, K, Ca, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Ba, Hf, Ta, W, Re, Os, Ir, Pt, Au, Hg, Tl, Pb, Ce, Pr, Nd, Pm, Sm, Eu, Gd, Tb, Dy, Ho, Er, Tm, Yb, Lu, Th, Pa, U, Np and Am, $Z^1$ to $Z^6$ independently represent a hydroxyl group, an alkoxy group having 1 to 18 carbon atoms, or a phenyl group, and Ar represents at least one aryl group selected from the formulas (2) to (12)

[Chemical Formula 8]

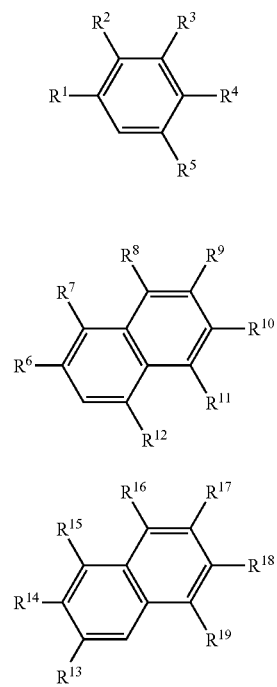

(2)

(3)

(4)

-continued

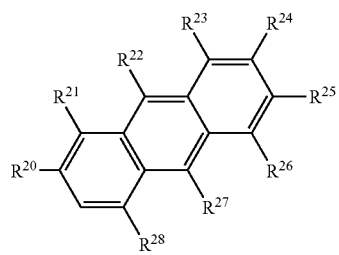
(5)

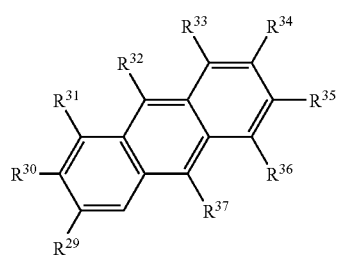
(6)

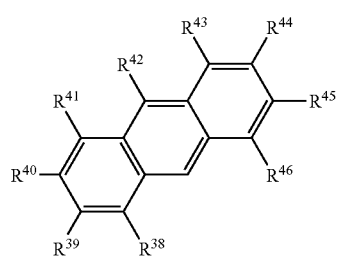
(7)

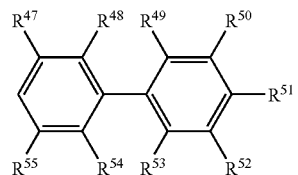
(8)

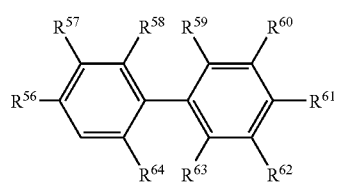
(9)

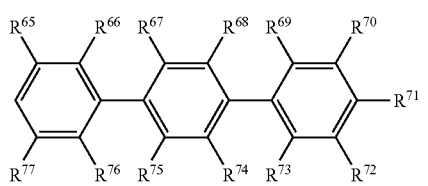
(10)

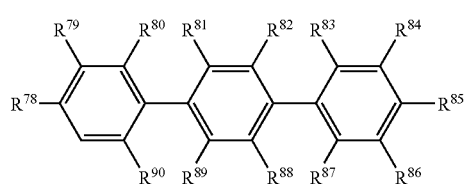
(11)

-continued

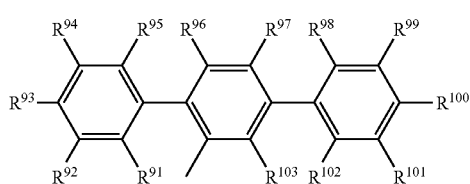 (12)

in the formulas (2) to (12), $R^1$ to $R^{103}$ independently represent a hydrogen atom, a halogen atom, a hydroxyl group, an amino group, a silanol group, a thiol group, a carboxyl group, a phosphoric group, a phosphoric ester group, an ester group, a thioester group, an amide group, a nitro group, a monovalent hydrocarbon group, an organooxy group, an organoamino group, an organosilyl group, an organothio group, an acyl group or a sulfone group)];

5. A phthalocyanine compound, characterized by being represented by the formula (16)

[Chemical Formula 9]

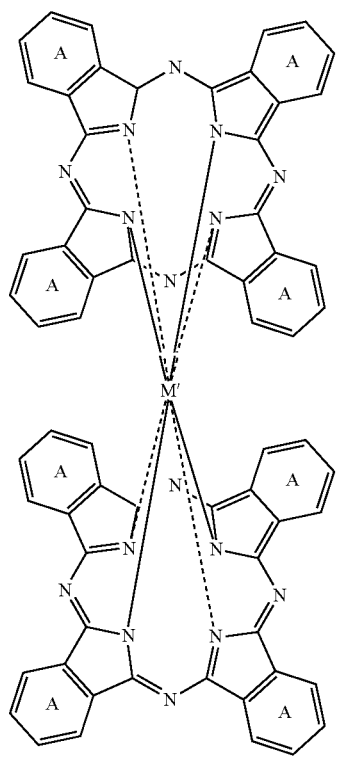 (16)

[wherein M' represents a lanthanoid or actinoid forming a double nucleus structure,

[Chemical Formula 10]

represents an aryl group represented by the formula (17) or (18) (provided that at lest one is an aryl group represented by the formula (17)),

[Chemical Formula 11]

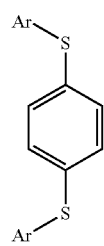 (17)

(in the formula (17), $Z^1$ and $Z^2$ independently represent a hydroxyl group, an alkoxy group having 1 to 18 carbon atoms, or a phenyl group)

[Chemical Formula 12]

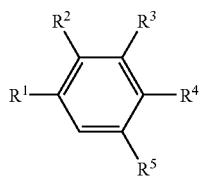 (18)

(in the formula (18), Ar represents at least one aryl group selected from the formulas (2) to (12)

[Chemical Formula 13]

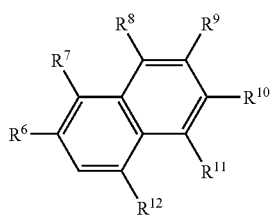 (2)

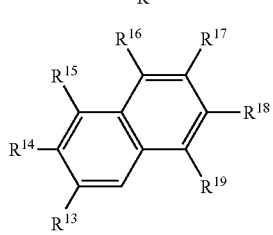 (3)

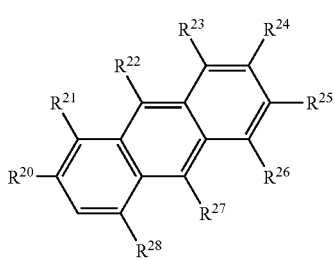 (4)

(5)

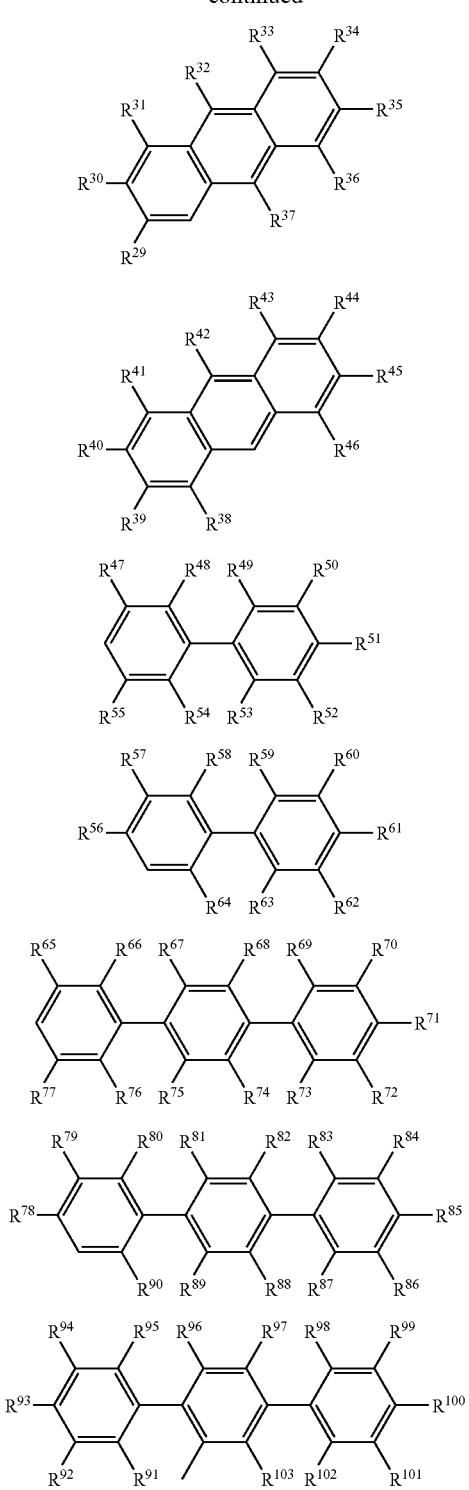

(in the formulas (2) to (12), $R^1$ to $R^{103}$ independently represent a hydrogen atom, a halogen atom, a hydroxyl group, an amino group, a silanol group, a thiol group, a carboxyl group, a phosphoric group, a phosphoric ester group, an ester group, a thioester group, an amide group, a nitro group, a monovalent hydrocarbon group, an organooxy group, an organoamino group, an organosilyl group, an organothio group, an acyl group or a sulfone group)];

6. A composition including the phthalocyanine compound of any of 1 to 5;
7. A varnish including the phthalocyanine compound of any of 1 to 5;
8. An organic thin film obtained from the phthalocyanine compound of any of 1 to 5;
9. An organic thin film prepared from the varnish of 7;
10. An electronic device including at least one layer of the organic thin film of 8 or 9;
11. An organic solar cell including at least one layer of the organic thin film of 8 or 9;
12. A photoelectric conversion device including at least one layer of the organic thin film of 8 or 9; and
13. An energy storage device including at least one layer of the organic thin film of 8 or 9.

Advantageous Effects

Since the phthalocyanine compound of the invention has a phosphoric ester group and a thioaryl group in the molecule, it has good affinity for titania and ensures good adhesion with titania when formed as an organic film.

This compound has an absorption maximum wavelength in the vicinity of or in the near-infrared region, exhibits high solubility in organic solvents and is able to form a uniform thin film according to a variety of wet processes.

Accordingly, the phthalocyanine compound of the invention is useful as one of members of electronic devices and particularly, an organic solar cell. When the phthalocyanine compound of the invention is used in such applications as mentioned above, it becomes possible to stably, inexpensively provide an organic solar cell whose photoelectric efficiency is good.

BRIEF DESCRIPTION OF DRAWINGS

FIG. 1 is a chart showing UV-VIS spectra of phthalocyanine compounds obtained in Examples 2, 6, 10 and Comparative Example 1.

BEST MODE FOR CARRYING OUT THE INVENTION

The invention is described hereinbelow in more detail.

In the phthalocyanine compounds represented by the formulas (1) and (13) to (16), Ar is an aryl group represented by the formulas (2) to (12) and $R^1$ to $R^{103}$ independently represent a hydrogen atom, a halogen atom, a hydroxyl group, an amino group, a silanol group, a thiol group, a carboxyl group, a phosphoric group, a phosphoric ester group, an ester group, a thioester group, an amide group, a nitro group, a monovalent hydrocarbon group, an organooxy group, an organoamino group, an organosilyl group, an organothio group, an acyl group or a sulfone group.

As a halogen atom, mention is made of fluorine, chlorine, bromine and iodine atoms.

The monovalent hydrocarbon group includes: an alkyl group such as a methyl group, an ethyl group, a propyl group, a butyl group, a t-butyl group, a hexyl group, an octyl group, a decyl group or the like; a cycloalkyl group such as a cyclopentyl group, a cyclohexyl group or the like; a bicycloalkyl group such as a bicyclohexyl group or the like; an alkenyl group such as a vinyl group, a 1-propenyl group, a 2-propenyl group, an isopropenyl group, a 1-methyl-2-propenyl group, a 1 or 2 or 3-butenyl group, a hexenyl group or the like; an aryl group such as a phenyl group, a xylyl group, a tolyl group, a biphenyl group, a naphthyl group or the like; or an aralkyl group such as a benzyl group, a phenylethyl group, a phenylcyclohexyl group or the like.

It will be noted that part or all of the hydrogen atoms of these monovalent hydrocarbon groups may be substituted with a hydroxyl group, a halogen atom, an amino group, a silanol group, a thiol group, a carboxyl group, a sulfone group, a phosphoric group, a phosphoric ester group, an ester group, a thioester group, an amide group, a nitro group, an organooxy group, an organoamino group, an organosilyl group, an organothio group, an acyl group, an alkyl group, a cycloalkyl group, a bicycloalkyl group, an alkenyl group, an aryl group, an aralkyl group and the like.

The organooxy group includes an alkoxy group, an alkenyloxy group, an aryloxy group or the like. The alkyl moiety, alkenyl moiety and aryl moiety of these groups are those similar to the above-mentioned monovalent hydrocarbon groups.

The organoamino group includes: a phenylamino group; an alkylamino group such as a methylamino group, an ethylamino group, a propylamino group, a butylamino group, a pentylamino group, a hexylamino group, a heptylamino group, an octylamino group, a nonylamino group, a decylamino group, a laurylamino group or the like; a dialkylamino group such as a dimethylamino group, a diethylamino group, a dipropylamino group, a dibutylamino group, a dipentylamino group, a dihexylamino group, a diheptylamino group, a dioctylamino group, a dinonylamino group, a didecylamino group or the like; or a cyclohexylamino group, a morpholino group or the like.

The organosilyl group includes a trimethylsilyl group, a triethylsilyl group, a tripropylsilyl group, a tributylsilyl group, a tripentylsilyl group, a trihexylsilyl group, a pentyldimethylsilyl group, a hexyldimethylsilyl group, an octyldimethylsilyl group, a decyldimethylsilyl group or the like.

The organothio group includes an alkylthio group such as a methylthio group, an ethylthio group, a propylthio group, a butylthio group, a pentylthio group, a hexylthio group, a heptylthio group, an octylthio group, a nonylthio group, a decylthio group, a laurylthio group or the like.

The acyl group includes a formyl group, an acetyl group, a propionyl group, a butyryl group, an isobutyryl group, a valeryl group, an isovaleryl group, a benzoyl group or the like.

The phosphoric ester group includes —P(O)(OQ$^1$)(OQ$^2$).
The ester group includes —C(O)OQ$^1$ or —OC(O)Q$^1$.
The thioester group includes —C(S)OQ$^1$ or —OC(S)Q$^1$.
The amide group includes —C(O)NHQ$^1$, —NHC(O)Q$^1$, —C(O)NQ$^1$Q$^2$ or —NQ$^1$C(O)Q$^2$.

In the above formulas, Q$^1$ and Q$^2$ represent an alkyl group, an alkenyl group or an aryl group, examples of which include those similar to the above-indicated monovalent hydrocarbon group.

The number of the carbon atoms in the monovalent organosilyl group, organothio group, acyl group, phosphoric ester group, ester group, thioester group, amide group or the like may not be critical and generally ranges 1 to 20, preferably 1 to 8.

Of the above-mentioned substituent groups, a fluorine atom, a sulfone group, a substituted or unsubstituted organooxy group, an alkyl group and an organosilyl group are preferred.

It will be noted that "unsubstituted" means bonding of hydrogen atom. In the above-mentioned substituent groups, a cyclic moiety through mutual linkage of substituents may be included.

The above-indicated Ar should preferably be substituted with an electron-donating group or an electron-attracting group in order to permit an absorption maximum at an intended wavelength.

Specific examples of the aryl groups represented by the formulas (2) to (12) are those indicated below although not limitative thereto.

[Chemical Formula 14]

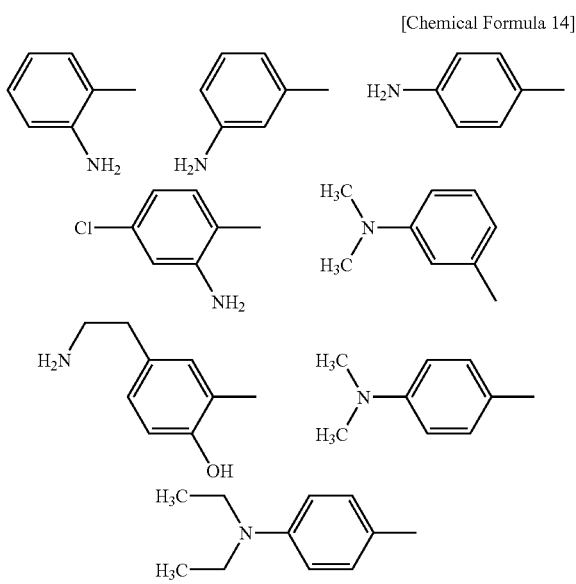

[Chemical Formula 15]

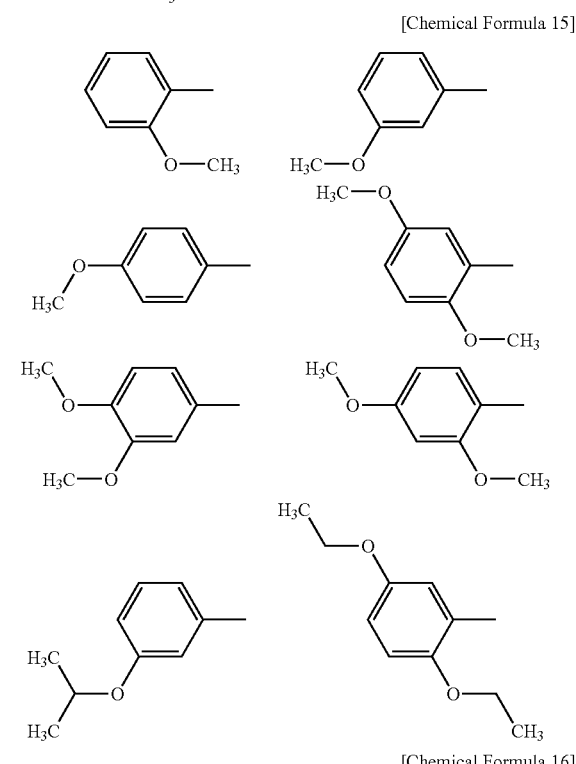

[Chemical Formula 16]

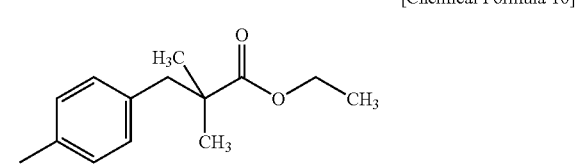

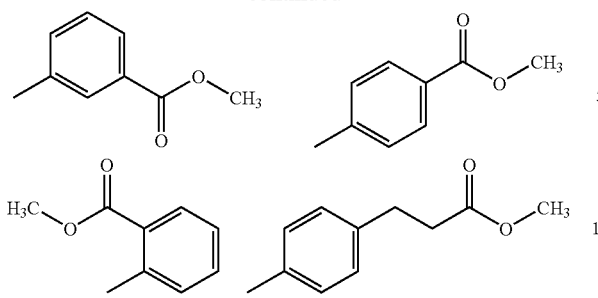
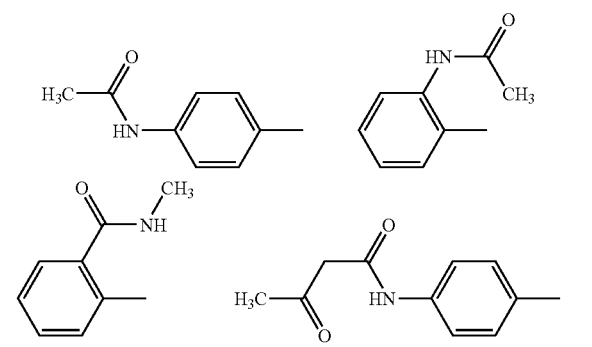
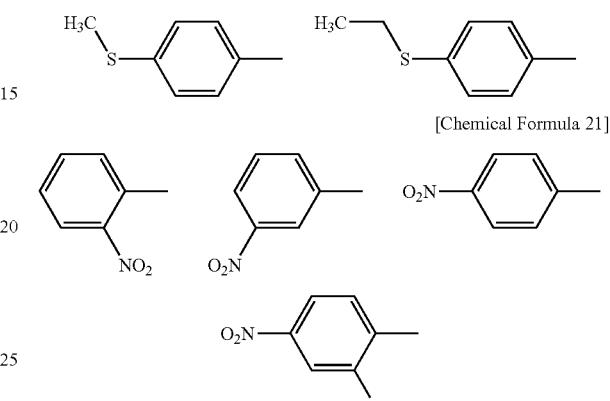
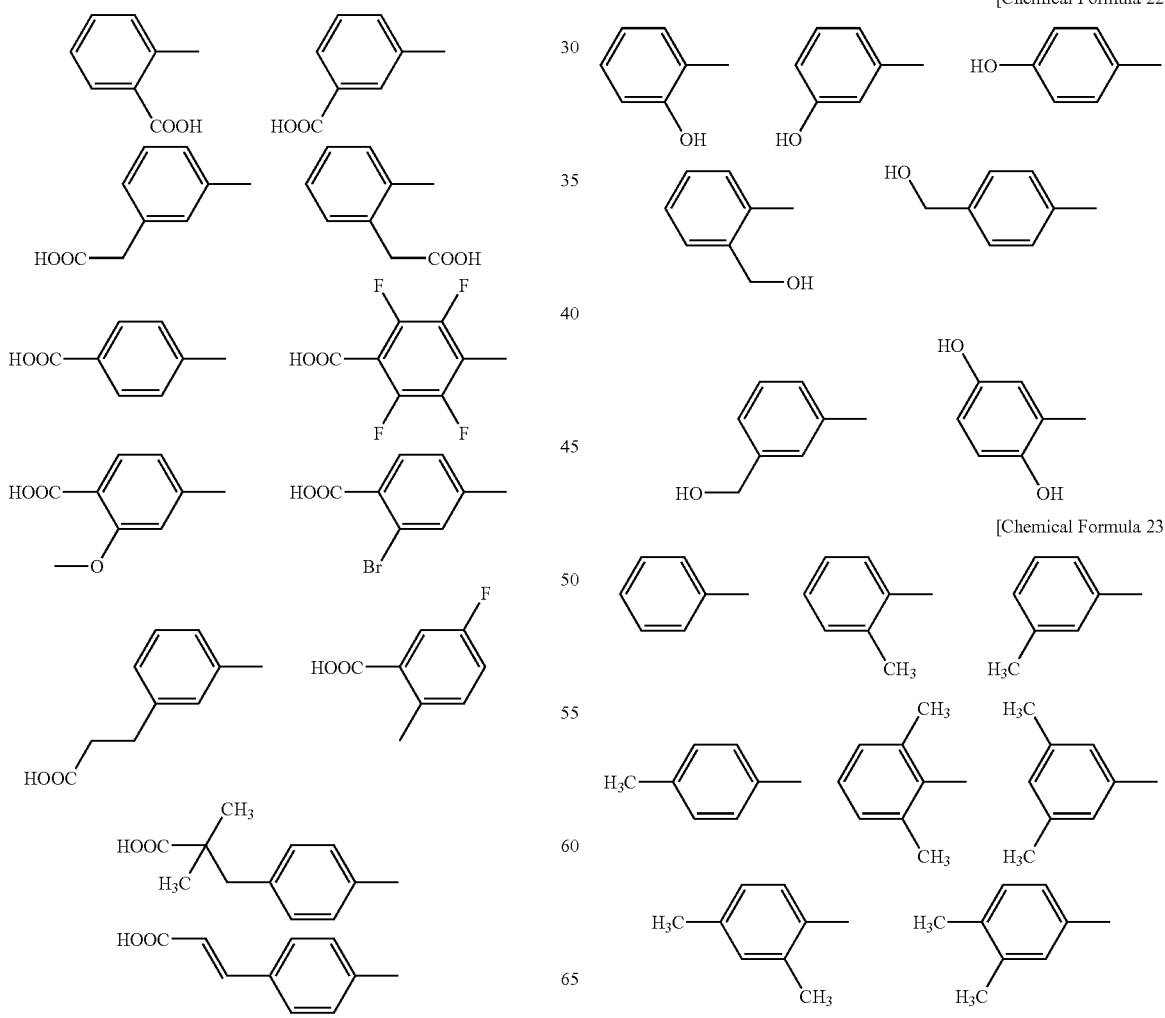

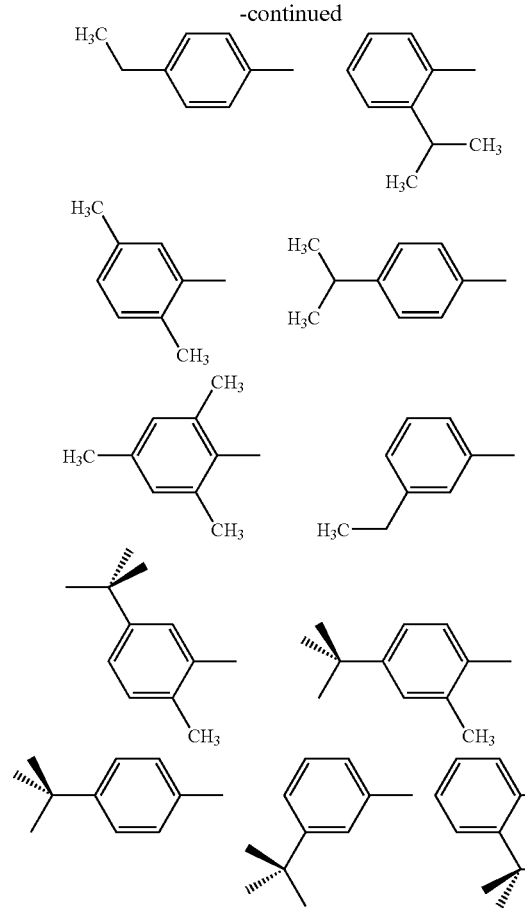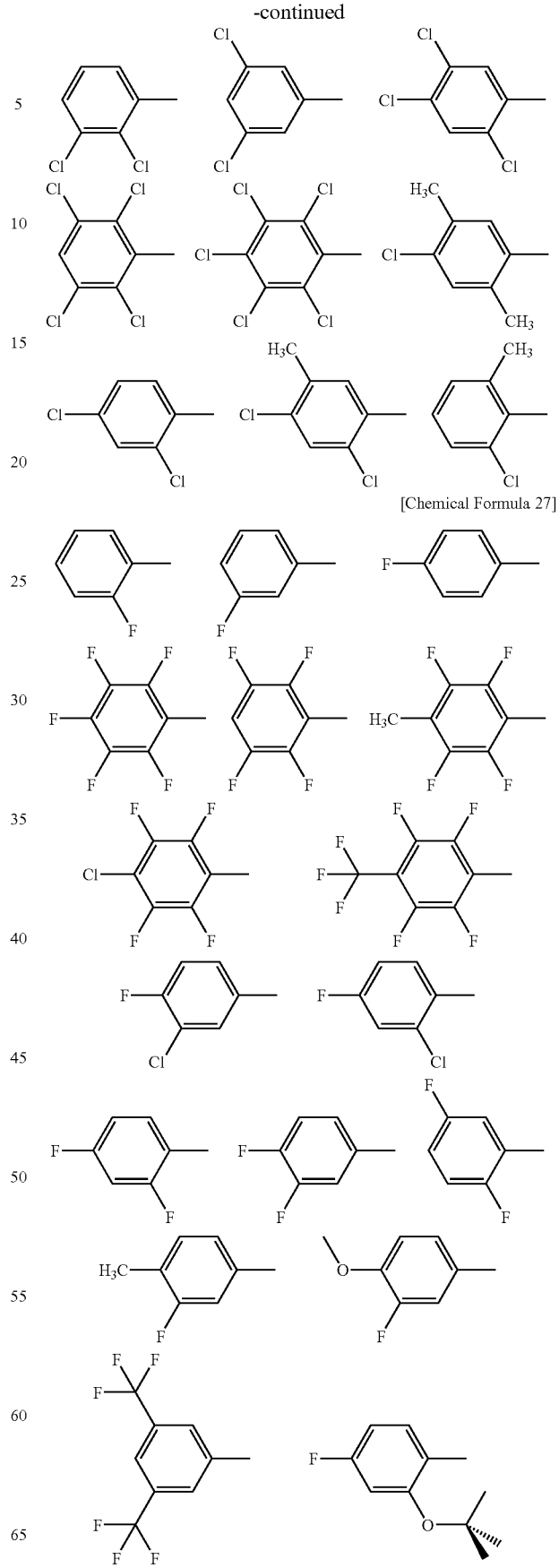

-continued
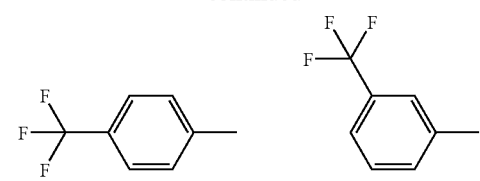
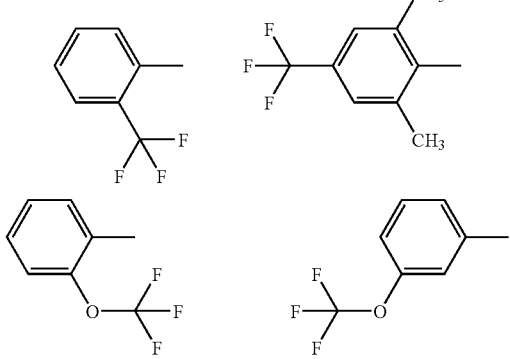
[Chemical Formula 28]
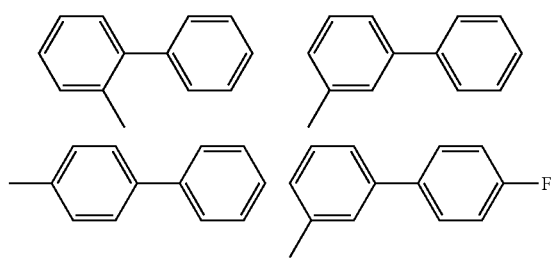
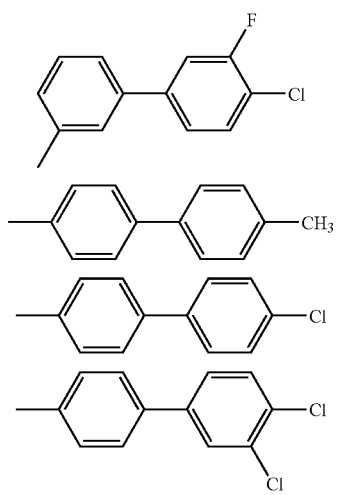
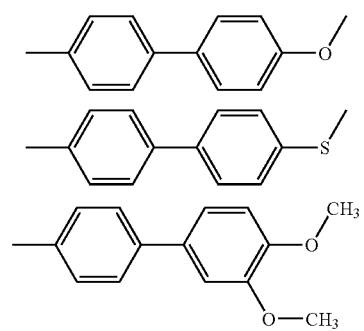
-continued
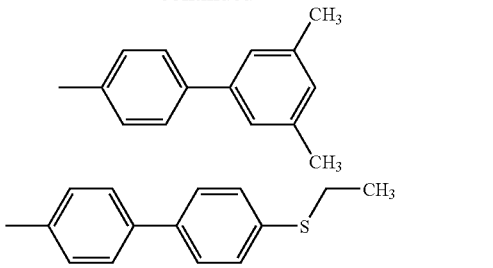
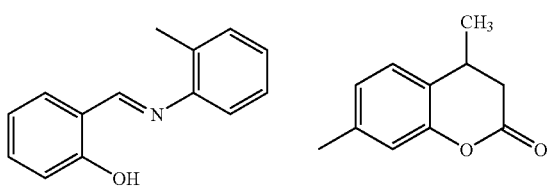
[Chemical Formula 29]
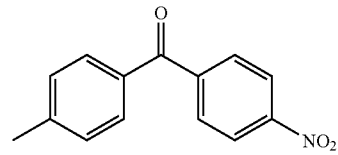
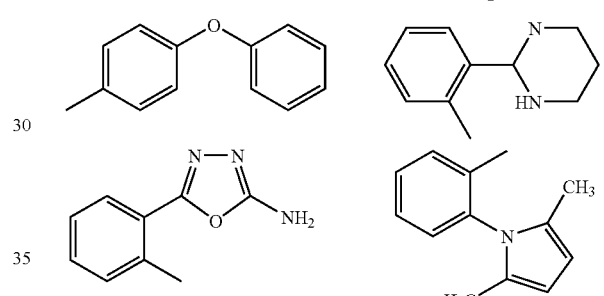
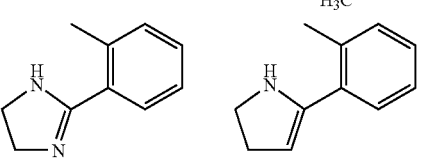
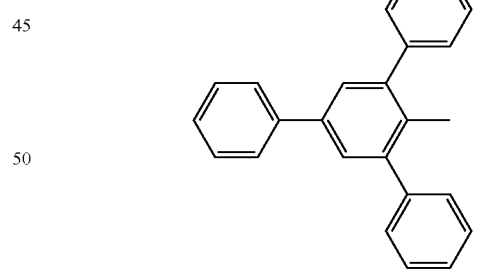
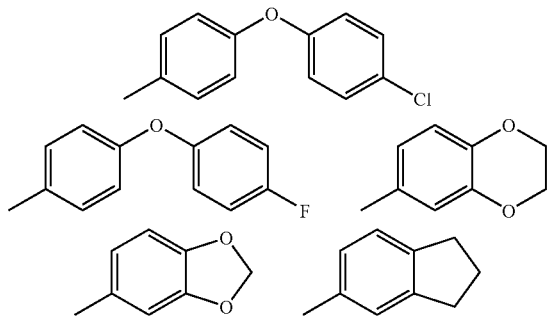

-continued

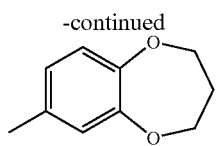

Z¹ to Z⁶ in the above formulas independently represent a hydroxyl group, an alkoxy group having 1 to 18 carbon atoms, or a phenyl group.

Specific examples of the alkoxy group having 1 to 18 carbon atoms include a methoxy group, an ethoxy group, an n-propoxy group, an i-propoxy group, and the like.

Of these, taking it into consideration to enhance affinity for titania, hydroxyl group is preferred.

In this case, Z¹ to Z⁶ may be all a hydroxyl group. If all are a hydroxyl group, solubility lowers. In order to ensure a solubility corresponding to a selected, appropriate solid concentration and organic film thickness, some of the hydroxyl groups may be replaced by an alkoxy group having 1 to 18 carbon atoms or a phenyl group.

M represents a hydrogen atom, or a central metal selected from Li, Be, Na, Mg, Al, Si, K, Ca, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Ba, Hf, Ta, W, Re, Os, Ir, Pt, Au, Hg, Tl, Pb, Ce, Pr, Nd, Pm, Sm, Eu, Gd, Tb, Dy, Ho, Er, Tm, Yb, Lu, Th, Pa, U, Np and Am.

Of these, it is preferred from the standpoint of deforming the porphyrazine ring for shifting toward a longer wavelength side to use those metals having a metal diameter greater than the central hole and including Co, Ni, Cu, Zn, Ga, Ge, As, Y, Zr, Nb, Mo, Tc, Ru, Rh, Pd, Ag, Cd, In, Sn, Sb, Ba, Hf, Ta, W, Re, Os, Ir, Pt, Au, Hg, Tl, Pb, Ce, Pr, Nd, Pm, Sm, Eu, Gd, Tb, Dy, Ho, Er, Tm, Yb, Lu, Th, Pa, U, Np and Am. In view of the relative ease in synthesis, it is more preferred to use Co, Ni, Cu, Zn, Ga, Ge, As, Y, Zr, Nb, Mo, Tc, Ru, Rh, Pd, Ag, Cd, In, Sn, Sb, Ba, Hf, Ta, W, Re, Os, Ir, Pt, Au, Hg, Tl and Pb.

M' represents a lanthanoid or actinoid forming a double nucleus structure and mention is made, for example, of Ce, Pr, Nd, Pm, Sm, Eu, Gd, Tb, Dy, Ho, Er, Tm, Yb, Lu, Th, Pa, U, Np and Am. Of these, it is preferred to use Eu, Er, Tm and Lu from the standpoint of the relative ease in synthesis with no safety problem.

Although the process of preparing the phthalocyanine compound represented by the formula (1) is not specifically limited, synthesis is possible by using, for example, a 3,6-bisthioaryl phthalonitrile compound and a dialkyl-(3,4-dicyanophenyl)phosphonate at a ratio corresponding to an intended phthalocyanine compound and subjecting them to cyclization in the presence of a basic catalyst and, if necessary, a desired central metal salt. In the synthesis, the use of a central metal salt capable of forming a double nucleus enables a phthalocyanine compound of a double nucleus structure represented by the formula (16) to be obtained.

The solvents usable in the reaction include 1-pentanol, 1-hexanol, 1-heptanol, 1-octanol, 1,2-dichlorobenzene, 1,2,4-trichlorobenzene, toluene, o-xylene, isopropyl alcohol, isobutanol, ethanol, methanol and the like although not limited thereto.

The reaction temperature is arbitrarily determined so far as such a temperature is at a level of cyclizing a phthalocyanine compound and is preferably within a range of 80 to 230° C. The reaction time is generally at 0.1 to 100 hours.

The phthalocyanine compound obtained by the above reaction can be purified by an ordinary purification technique including, for example, sublimation, column or recrystallization.

If a recrystallization technique is adopted, a solvent used therefor includes, for example, 1,4-dioxane, tetrahydrofuran, dichloromethane, toluene, chloroform, pyridine, ethanol, methanol or the like although not limited thereto.

The phthalocyanine compound of the invention as thus far illustrated can be used as a varnish (composition) by mixing with solvents.

The solvents used for the preparation of the varnish include, for example, water; and methanol, N,N-dimethylformamide, N,N-dimethylacetamide, N-methylpyrrolidone, 1,3-dimethyl-2-imidazolidinone, dimethylsulfoxide, γ-butyrolactone, chloroform, toluene, o-dichlorobenzene, 1,2,4-trichlorobenzene, 1-chloronaphthalene, dichloromethane, tetrahydrofuran, propylene glycol monomethyl ether, dimethyl ketone, methyl ethyl ketone, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol, hexylene glycol, butyl cellosolve, diethylene glycol diethyl ether, dipropylene glycol monomethyl ether, ethyl carbitol, diacetone alcohol, ethyl lactate and the like although not imitative thereto. These solvents may be used singly or in combination of two or more.

It will be noted that the phthalocyanine compound is preferably dispersed or dissolved uniformly in the varnish (composition) of the invention.

An organic thin film can be formed by coating the varnish described above onto a substrate and evaporating the solvent therefrom.

The coating technique of the varnish is not critical and includes a dipping method, a spin coating method, a transfer printing method, a roll coating method, a brushing method, an ink jet method, a spraying method or the like.

The manner of solvent evaporation is not critical and evaporation may be performed, for example, by use of a hot plate or an oven in an appropriate atmosphere, i.e. in air, in an inert gas such as nitrogen or the like, in vacuum, or the like. In this way, it becomes possible to obtain a thin film having a uniform surface.

The baking temperature is not critical on the condition that the solvent can be evaporated, and the evaporation is preferably made at 40 to 250° C. In this case, the temperature may be changed by two or more stages for the purposes of permitting a more uniform film to be formed and causing the reaction to proceed on a substrate.

The thickness of the organic thin film is not critical and is preferably at 5 to 200 nm when used as a charge injection layer in an organic EL device. Likewise, the thickness is preferably at 1 (monolayer) to 100 nm on use as a covering layer on titania of organic solar cells.

For the change of film thickness, there are used methods of changing a solid concentration in varnish, changing an amount of solution on a substrate upon coating, changing a surface energy by treatment of substrate, and the like.

Because the varnish of the invention can be formed as a film by coating onto a variety of substrates, it is useful to apply the varnish as a capacitor electrode protection film, an antistatic film, or organic films utilized for gas sensors, temperature sensors, humidity sensors, pressure sensors, optical sensors, radiation sensors, ion sensors, biosensors or field emission transistor sensors; organic films utilized for primary cells, secondary cells, fuel cells or polymer cells; and an electromagnetic shield film, a UV absorption film, a gas barrier film, or organic films used for optical information recording mediums or optical integrated circuits.

EXAMPLES

The invention is more particularly described by way of Examples and Comparative Examples and the invention should not be construed as being limited to the following Examples. It will be noted that measuring apparatus used in the Examples are just as described below.

[MS Spectrum]
Apparatus (FAB-MS): JMS-700T, made by JEOL Ltd.
[IR Spectrum]
Nexus 670, made by Nicolet Japan Corporation
[NMR Spectrum]
ECP300, made by JEOL Ltd.
[Elementary Analysis]
PE2400 Series II, made by Perkin Elmer Co., Ltd.
[Measurement of Film Thickness]
High accuracy microprofiler SUREFCORDER ET4000A, made by Kosaka Laboratory Ltd.
[Ionization Potential (Hereinafter Abbreviated as Ip)]
Photoelectric spectrometer AC-2, made by Riken Keiki Co., Ltd.
[UV-VIS Spectrum]
UV-3100PC, made by Shimadzu Corporation
[Adhesion Test]
SAICAS Model NM-04, made by Daipla Wintes Co., Ltd.

[1] Synthesis of Starting Compound

Synthetic Example 1

Synthesis of phthalonitrile-3,6-ditriflate (Hereinafter Abbreviated as PN-3,6-DOTf)

(Reaction Formula 1)

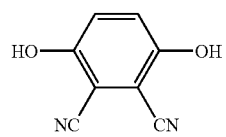

[Chemical Formula 30]

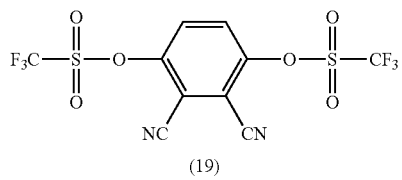

(19)

PN-3,6-DOTf represented by the formula (19) was prepared from 3,6-dihydroxyphthalonitrile according to the following procedure (reaction formula 1) described at pages 2064 to 2065 of Chemical Communications, United Kingdom, 2003.

In a 500 ml three-necked flask, 4.8039 g (30 mmols) of 3,6-dihydroxyphthalonitrile, 100 ml of methylene chloride and 5.9325 g (75 mmols, 2.5 equivalents) of pyridine were placed under nitrogen atmosphere, followed by cooling down to −78° C. on a dry ice-acetone bath while stirring.

Next, 21.159 g (75 mmols, 2.5 equivalents) of trifluoromethanesulfonic acid anhydride was dropped with an inner-pressure equilibrium dropping funnel in 30 minutes so that the temperature in the system did not rise over −70° C. After completion of the dropping, the dry ice-acetone bath was removed, followed by warming to room temperature (23° C.) and stirring at the temperature for 24 hours.

After completion of the reaction, the reaction solution was poured into 600 ml of pure water (6 equivalents relative to methylene chloride), followed by liquid-liquid extraction with 100 ml of methylene chloride five times. A separated organic phase was successively washed with 200 ml of pure water, 200 ml of a 2% hydrochloric acid aqueous solution, 200 ml of pure water, 1000 ml of a saturated saline solution and 200 ml of pure water in this order, followed by dehydration with magnesium sulfate. After filtration of the magnesium sulfate, the methylene chloride was distilled off with an evaporator. The resulting crude product was recrystallized from methylene chloride to obtain 6.3546 g (yield: 50%) of PN-3,6-DOTf in the form of colorless, transparent rod-shaped crystals. The thus obtained crystals were identified from IR and NMR spectra with respect to the structure thereof and confirmed as PN-3,6-DOTf.

IR (m$^{-1}$): 3115 (Arom, $v_{C-H}$), 2250 ($v_{C-N}$), 1601, 1472, 1439 ($v_{C-C}$), 1134 ($v_{S-O}$).

$^1$H-NMR (ppm/DMSO-d$_6$): δ 8.44 (s, 2H).

Synthetic Example 2

Synthesis of 3,6-bis(thiophenylmethyl)phthalonitrile (Hereinafter Abbreviated as 3,6-BTPMPN)

(Reaction Formula 2)

[Chemical Formula 31]

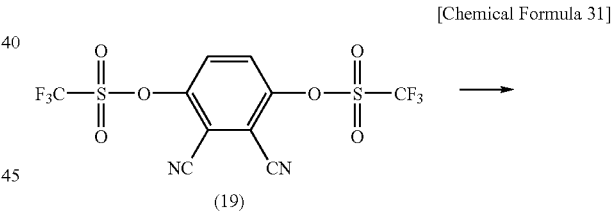

(19)

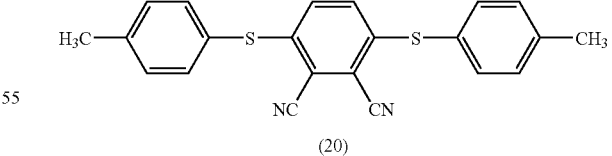

(20)

3,6-BTPMPN represented by the formula (20) was synthesized according to the following procedure (Reaction Formula 2) using PN-3,6-DOTf, obtained in Synthetic Example 1, as a starting material.

It will be noted that synthesis from PN-3,6-DOTf may be possible while referring to Chemical Communications, United Kingdom, 2003, pp. 2064-2065, but not limited thereto.

In a 100 ml of eggplant flask, 0.8485 g (2 mmols) of PN-3,6-DOTf, 1.1610 g (8.4 mmols, 4.2 equivalents) of potassium carbonate and 15 ml of DMSO were placed and stirred. Next, 0.4968 g (4 mmols, 2 equivalents) of p-toluenethiol was added to the flask, followed by purging the flask with nitrogen and reaction under stirring at 23° C. for 24 hours.

After completion of the reaction, the reaction solution was poured into 300 ml of pure water (20 equivalents relative to DMSO), followed by liquid-liquid extraction with 100 ml of methylene chloride five times. A separated organic phase was dehydrated with magnesium sulfate and, after filtration of the magnesium sulfate, the methylene chloride was distilled off with an evaporator. The resulting crude product was washed three times with 50 ml of methanol by decantation, followed by recrystallization from methylene chloride to obtain 0.1770 g (yield: 23%) of a light yellow solid of 3,6-BTPMPN. The thus obtained crystals were identified from IR and NMR spectra with respect to the structure thereof and confirmed as 3,6-BTPMPN.

IR (cm$^{-1}$): 3050 (Arom, $v_{C-H}$), 2970 ($v_{C-H}$), 2218 ($v_{C-N}$), 1600, 1535, 1490, 1435 ($v_{C-C}$), 1210, 809 ($\delta_{C-H}$).

$^1$H-NMR (ppm/DMSO-d$_5$): δ 7.57 (d, 4H), 7.46 (d, 4H), 7.35 (s, 2H), 2.66 (tt, 6H).

Synthetic Example 3

Synthesis of 4-bromophthalamide (Hereinafter Abbreviated as 4-BPA)

(Reaction Formula 3)

[Chemical Formula 32]

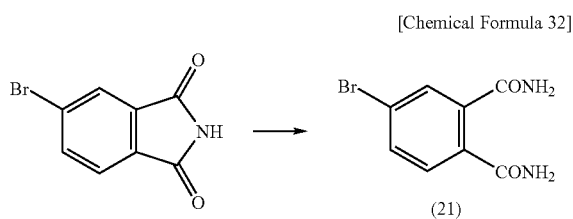

(21)

4-BPA represented by the formula (21) was synthesized from 4-bromophthalimide (hereinafter abbreviated as 4-BPI) according to the following procedure (reaction formula 3) with reference to Journal of Heterocyclic Chemistry, 1995, pp. 495-498.

In a 100-ml eggplant flask, 27.8017 g (0.123 mols) of 4-BPI and 60 ml of 20% ammonia water were placed followed by reaction under stirring at 23° C. for 48 hours. After completion of the reaction, the reaction solution in the form of a white suspension was allowed to stand at 0° C. for one hour, followed by filtration under reduced pressure. The resulting white solid was dried in a reduced pressure dryer at 23° C. or 24 hours to obtain 29.90 g (yield: 75%) of a white powder of 4-BPA. The thus obtained white powder was subjected to identification of the structure thereof from NMR spectra and confirmed as 4-BPA.

$^1$H-NMR (ppm/DMSO-d$_6$): δ 7.84 (s, 1H), 7.78 (s, 1H), 7.67 (d, 1H), 7.65 (d, 1H), 7.62 (d, 1H), 7.43 (s, 1H), 7.40 (s, 1H).

Synthetic Example 4

Synthesis of 4-bromophthalonitrile (Hereinafter Abbreviated as 4-BPN)

(Reaction Formula 4)

[Chemical Formula 33]

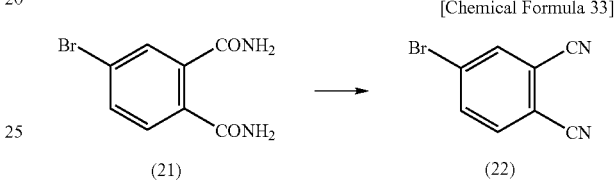

(21)                    (22)

4-BPN represented as the formula (22) was synthesized from 4-BPA, obtained in Synthetic Example 3, according to the following procedure with reference to Synthesis, 1993, pp. 194-196.

In a 200-ml eggplant flask, 100 ml of dried N,N-dimethylformamide was placed in which 70 ml of thionyl chloride was dropped so as not to allow a rise of temperature over 5° C. while stirring in an ice bath of 0° C. After completion of the dropping, the mixture was allowed to stand at 0° C. for two hours.

Next, 20.9032 g (0.086 mols) of 4-BPA was gently added to in the form of powder so as not to permit a rise of temperature over 5° C. Subsequently, while keeping the reaction temperature within 0 to 5° C., the reaction was carried out for five hours, followed by removing the ice bath and raising the temperature up to 23° C. and carrying out the reaction for 24 hours while keeping the temperature.

After completion of the reaction, the reaction solution in the form of a whitish yellow suspension was gently poured into a one-liter beaker in which 300 g of ice pieces was placed. Precipitated whitish yellow crystals were filtrated under reduced pressure, washed with 100 ml of pure water and further washed with 100 ml of methanol.

Ten times by weight of methanol was added to the whitish yellow crude product, which was completely dissolved by use of an oil bath and stored at 23° C. for recrystallization. The resulting white crystals were dried for 24 hours with a reduced pressure dryer to obtain 17.80 g (yield: 80%) of 4-BPN as white crystals. The thus obtained white crystals were subjected to identification of the structure thereof from NMR spectra and confirmed as 4-BPN.

$^1$H-NMR (ppm/CDCl$_3$): 7.96 (dd, 1H), 7.90 (dd, 1H), 7.67 (d, 1H).

Synthetic Example 5

Synthesis of diethyl-(3,4-dicyanophenyl)phosphonate (Hereinafter Abbreviated as 4-P=O(OEt)$_2$PN)

(Reaction Formula 5)

[Chemical Formula 34]

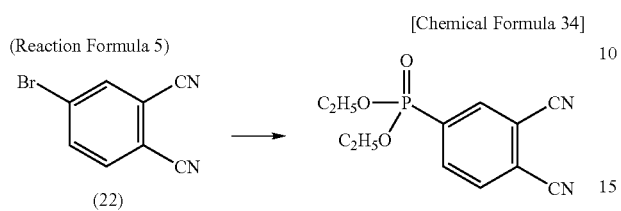

(Reaction Formula 6)

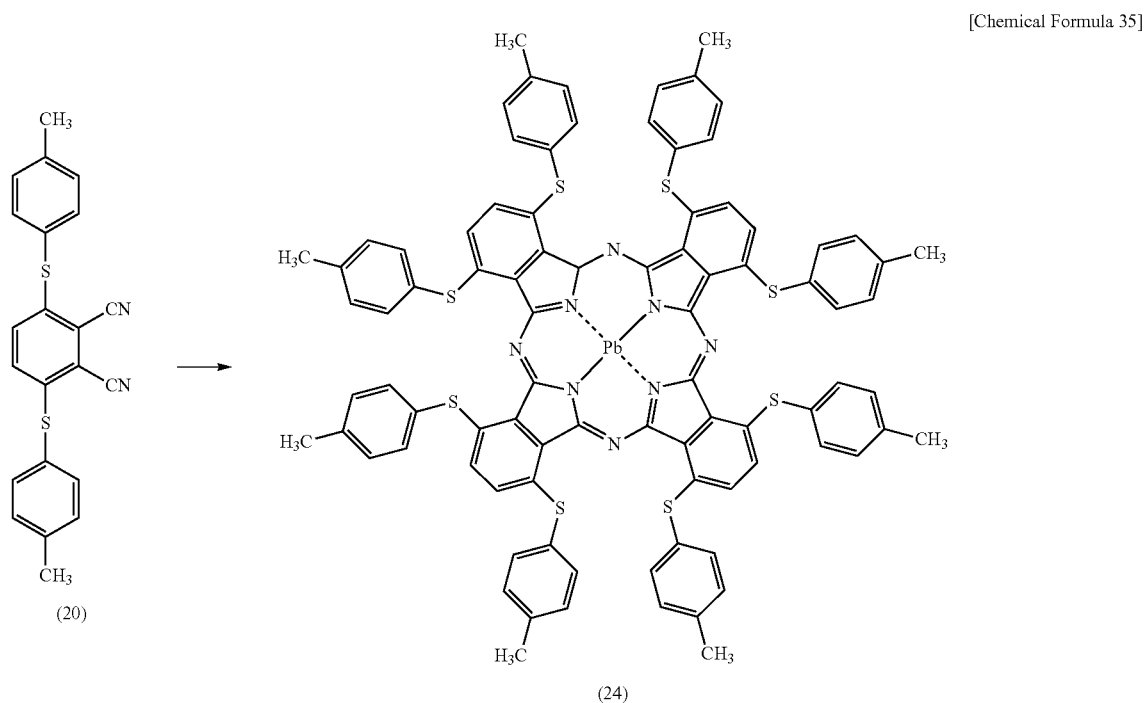

4-P=O(OEt)$_2$PN represented as the formula (23) was synthesized from 4-BPN, obtained in Synthetic Example 4, according to the following procedure (reaction formula 5) with reference to Helvetica Chimica Acta, 2004, pp. 825-844.

In a 50-ml eggplant flask, 3.1055 g (15 mmols) of 4-BPN was placed and the system was purged with nitrogen, followed by adding 0.1944 g (0.15 mmols, 0.1 equivalents relative to 4-BPN) of nickel (II) chloride and further purging the system with nitrogen.

Next, 3.42 ml (d=0.97, 20 mmols, 1.3 equivalents relative to 4-BPN) of triethyl phosphite was added by means of a syringe on an oil bath of 160° C., followed by reaction for one hour while keeping the temperature at 160° C. under stirring.

After completion of the reaction, the crude product obtained as a reddish green viscous liquid was purified by use of silica gel column chromatography using silica gel 7734 (0.063 to 0.02 mm), made by Merck Co., & Inc., as a solid phase and chloroform as an eluate to obtain 2.65 g (yield: 67%) of a colorless transparent liquid of 4-P=O(OEt)$_2$PN. The thus obtained colorless transparent liquid was identified from NMR with respect to the structure thereof and confirmed as 4-P=O(OEt)$_2$PN.

$^1$H-NMR (ppm/CDCl$_3$): 8.19 (s, 1H), 7.94 (d, 1H), 7.77 (d, 1H), 4.18 (m, 4H), 1.35 (tt, 6H).

[2] Synthesis of Phthalocyanine Compound

Comparative Example 1

Lead (II) 1,4,8,11,15,18,22,25-octathiophenylmethyl-phthalocyaninato (hereinafter abbreviated as OTPM-PbPC)

[Chemical Formula 35]

OTPM-PbPC represented as the formula (24) was synthesized from 3,6-BTPMPN according to the following procedure (reaction formula 6) in conformity with the Linstead process as in Journal of Japan Society of Color Material, Japan, 2002, Vol. 75, pp. 214-220.

In a 20-ml eggplant flask, 0.0931 g (0.25 mmols) of 3,6-BTPMPN, 0.0174 g (0.0625 mmols, 0.25 equivalents) of lead (II) chloride, 10 ml of 1-pentanol and 0.2 ml of 1,8-diazabicyclo[5,4,0]-7-undecene (hereinafter abbreviated as DBU) were placed and refluxed at 160° C. for seven hours.

After completion of reaction, the reaction solution was cooled down to room temperature and poured into 200 ml of methanol. The resulting precipitated solid was washed by decantation twice with 100 ml of pure water and twice with 100 ml of methanol in this order.

The crude product was purified by silica gel column chromatography using silica gel 7734 (0.063 to 0.02 mm), made by Merck Co., & Inc., as a solid phase and toluene as an eluate to obtain 0.02 g (yield: 18%) of a reddish black solid.

Comparative Example 2

Ruthenium 1,4,8,11,15,18,22,25-octathiophenylmethyl-phthalocyaninato (Hereinafter Abbreviated as OTPM-RuPC)

[Chemical Formula 36]

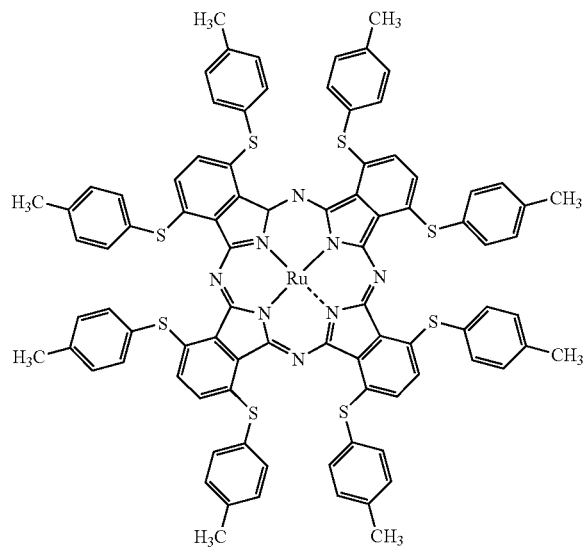

(25)

OTPM-RuPC represented as the formula (25) was synthesized in the same manner as in Comparative Example 1 except that the central metal was changed to ruthenium (Ru).

Example 1

Synthesis of lead 1,4,8,11,15,18-hexathiophenylmethyl-phthalocyaninato phosphoric ester (Hereinafter Abbreviated as $PbPC_{3:1}$)

[Chemical Formula 37]

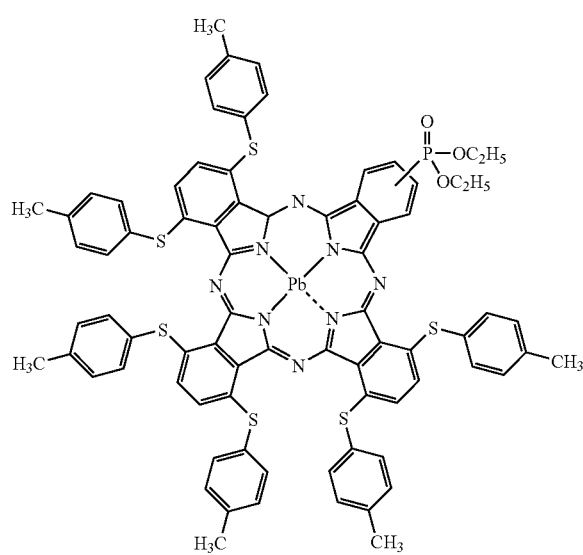

(26)

$PbPC_{3:1}$ represented as the formula (26) was synthesized according to the following procedure.

In a 20-ml eggplant flask, 0.0698 g (0.1875 mmols) of 3,6-BTPMPN, 0.0165 g (0.0625 mmols) of 4-P=O(OEt)$_2$ PN, 0.0174 g (0.0625 mmols, 0.25 eq.) of lead (II) chloride, 10 ml of 1-pentanol and 0.2 ml of DBU were placed and refluxed at 160° C. for seven hours.

After completion of reaction, the reaction solution was cooled down to room temperature and poured into 200 ml of methanol. The resulting precipitated solid was washed by decantation twice with 100 ml of pure water and twice with 100 ml of methanol in this order.

The crude product was purified by silica gel column chromatography using silica gel 7734 (0.062 mm to 0.02 mm), made by Merck Co., & Inc., as a solid phase and chloroform as an eluate to obtain 0.0475 g (yield: 52%) of a brown solid.

Example 2

Synthesis of $bPC_{3:1}$—OH

[Chemical Formula 38]

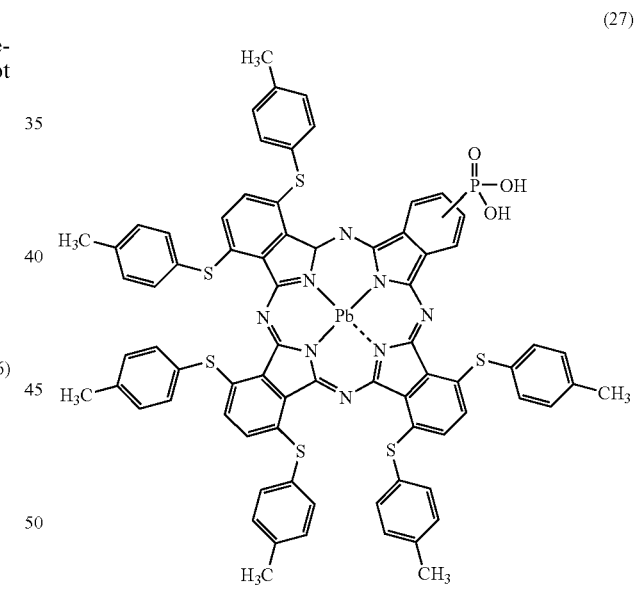

(27)

$PbPC_{3:1}$—OH represented as the formula (27) was synthesized according to the following procedure.

By use of an oil bath, 0.02 g (0.0142 mmols) of $PbPC_{3:1}$ obtained in Example 1 was subjected to reaction in 10 ml of concentrated hydrochloric acid at 100° C. for 24 hours.

After the reaction, the resulting precipitated blackish brown solid was filtrated by suction and washed with pure water. The washing with pure water was continued until the pH of the filtrate reached 7.0.

Thereafter, the solid was dried with a reduced pressure dryer at 23° C. for 24 hours to obtain 0.0190 g (yield: 95%) of PbPC$_{3:1}$—OH as a blackish brown solid.

Example 3

Synthesis of ruthenium 1,4,8,11,15,18-hexathiophenylmethyl-phthalocyaninato phosphoric ester (Hereinafter Abbreviated as RuPC$_{3:1}$)

In the same manner as in Example 1 except that the central metal was changed to ruthenium (Ru), 0.0412 g (yield: 44%) of a black solid of RuPC$_{3:1}$ was obtained.

Example 4

Synthesis of RuPC$_{3:1}$—OH

In the same manner as in Example 2, RuPC$_{3:1}$ obtained in Example 3 was hydroxylated to obtain 0.0194 g (yield: 97%) of a brown solid of RuPC$_{3:1}$—OH.

Example 5

Synthesis of lead tetrathiophenylmethyl-phthalocyaninato phosphoric ester (Hereinafter Abbreviated as PbPC$_{2:2}$)

[Chemical Formula 39]

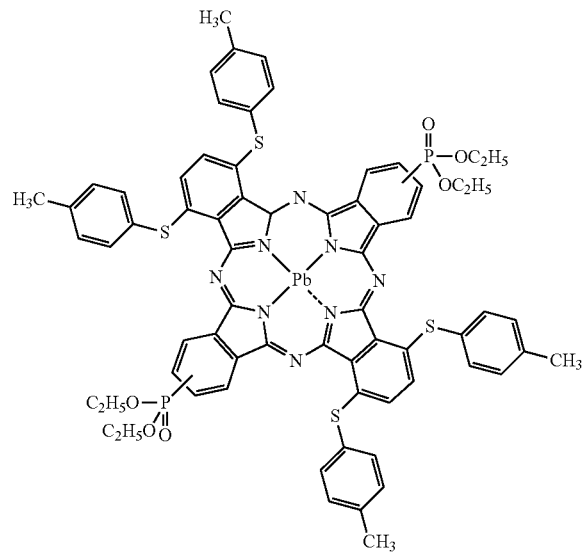

(28)

PbPC$_{2:2}$ represented as the formula (28) was synthesized according to the following procedure.

In a 20 ml eggplant flask, 0.0466 g (0.1250 mmols) of 3,6-BTPMPN, 0.0330 g (0.1250 mmols) of 4-P=O(OET)$_2$PN, 0.0174 g (0.0625 mmols, 0.25 equivalents) of lead (II) chloride, 10 ml of 1-pentanol and 0.2 ml of DBU were placed and refluxed at 160° C. for seven hours.

After completion of reaction, the reaction solution was cooled down to room temperature and poured into 200 ml of methanol. The resulting precipitated solid was washed by decantation twice with 100 ml of pure water and twice with 100 ml of methanol in this order.

The crude product was purified with silica gel column chromatography using silica gel 7734 (0.063-0.02 mm), made by Merck Co., & Inc., as a solid phase and chloroform as an eluate to obtain 0.0428 g (yield: 50%) of a greenish black solid of PbPC$_{2:2}$.

Example 6

Synthesis of PbPC$_{2:2}$—OH

[Chemical Formula 40]

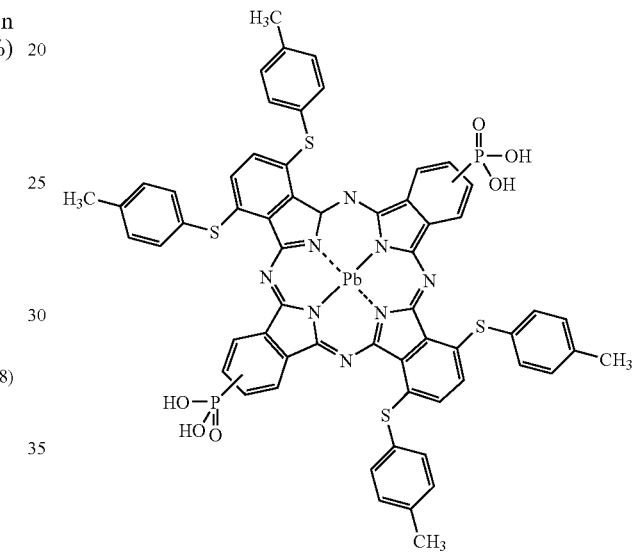

(29)

PbPC$_{2:2}$—OH represented as the formula (29) was synthesized according to the following procedure.

By use of an oil bath, 0.02 g (0.0159 mmols) of PbPC$_{2:2}$ was reacted in 10 ml of concentrated hydrochloric acid at 100° C. for 24 hours.

After the reaction, the resulting precipitated greenish brown solid was filtrated by suction and washed with pure water. The washing with pure water was continued until the pH of the filtrate reached 7.0.

Thereafter, the solid was dried with a reduced pressure dryer at 23° C. for 24 hours to obtain 0.0186 g (yield: 93%) of a greenish brown solid of PbPC$_{2:2}$—OH.

Example 7

Synthesis of ruthenium tetrathiophenylmethyl-phthalocyaninato phosphoric ester (Hereinafter Abbreviated as RuPC$_{2:2}$)

In the same manner as in Example 5 except that the central metal was changed to ruthenium (Ru), 0.0431 g (yield: 49%) of a black solid of RuPC$_{2:2}$ was obtained.

Example 8

Synthesis of $RuPC_{2:2}$—OH

In the same manner as in Example 6, $RuPC_{2:2}$ obtained in Example 7 was hydroxylated to obtain 0.0190 g (yield: 95%) of a brown solid of $RuPC_{2:2}$—OH.

Example 9

Synthesis of lead dithiophenylmethyl-phthalocyaninato phosphoric ester (Hereinafter Abbreviated as $PbPC_{1:3}$)

[Chemical Formula 41]

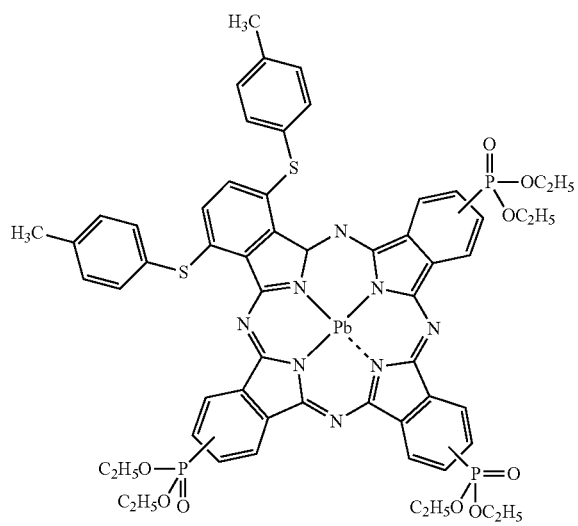

(30)

$PbPC_{1:3}$ represented by the formula (30) was synthesized according to the following procedure.

In a 20 ml eggplant flask, 0.0233 g (0.0625 mmols) of 3,6-BTPMPN, 0.0495 g (0.1875 mmols) of 4-P=O(OEt)$_2$, 0.0174 g (0.0625 mmols, 0.25 equivalents) of lead (II) chloride, 10 ml of 1-pentanol and 0.2 ml of DBU were placed and refluxed at 160° C. for seven hours.

After completion of reaction, the reaction solution was cooled down to room temperature and poured into 200 ml of methanol. The resulting precipitated solid was washed by decantation twice with 100 ml of pure water and twice with 100 ml of methanol.

The crude product was purified with silica gel column chromatography using silica gel 7734 (0.063-0.02 mm), made by Merck Co., & Inc., as a solid phase and chloroform as an eluate thereby obtaining 0.0471 g (yield: 59%) of a bluish black solid of $PbPC_{1:3}$.

Example 10

Synthesis of $PbPC_{1:3}$—OH

[Chemical Formula 42]

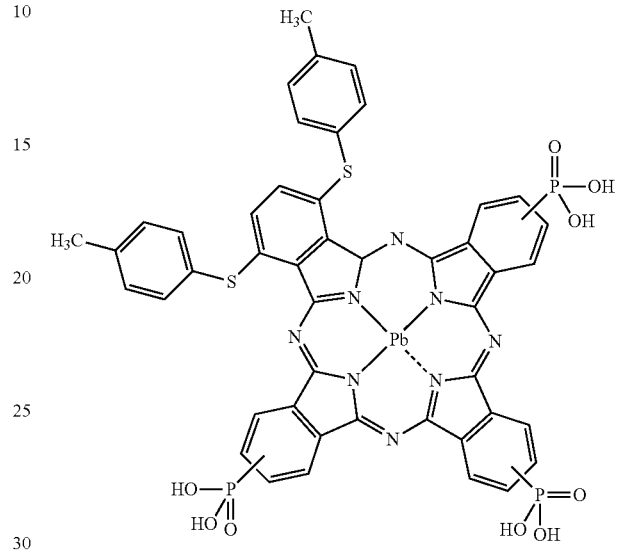

(31)

$PbPC_{1:3}$—OH represented as the formula (31) was synthesized according to the following procedure.

By use of an oil bath, 0.02 g (0.0180 mmols) of $PbPC_{1:3}$ was reacted in 10 ml of concentrated hydrochloric acid at 100° C. for 24 hours.

After the reaction, the resulting precipitated blackish blue solid was filtrated by suction and washed with water. The washing with water was continued until the pH of the filtrate reached 7.0.

Thereafter, the solid was dried with a reduced pressure dryer at 23° C. for 24 hours to obtain 0.0178 g (yield: 89%) of a blackish blue solid of $PbPC_{1:3}$—OH.

Example 11

Synthesis of ruthenium dithiophenylmethyl-phthalocyaninato phosphoric ester (hereinafter abbreviated as $RuPC_{1:3}$)

In the same manner as in Example 9 except that the central metal was changed to Ru, 0.0518 g (yield: 63%) a black solid of $RuPC_{1:3}$ was obtained.

Example 12

Synthesis of $RuPC_{1:3}$—OH

In the same manner as in Example 10, $RuPC_{1:3}$ obtained in Example 11 was hydroxylated to obtain 0.0174 g (yield: 87%) of a brown solid of $RuPC_{1:3}$—OH.

The results of analyses of the phthalocyanine compounds synthesized in the foregoing Examples 1 to 12 and Comparative Examples 1 and 2.

TABLE 1

| Entry | Abbreviation | Compositional formula | M.W. [g/mol] | FAB-MS [m/z] | | Elementary analysis [%] |
|---|---|---|---|---|---|---|
| Comparative Example 1 | OTPM-PbPC | $C_{88}H_{65}N_8PbS_8$ | 1698.24 | 1698 | Calcd.: | C, 62.24; H, 3.86; N, 6.60; S, 15.11 |
| | | | | | Found: | C, 62.20; H, 3.85; N, 6.58; S, 15.10 |
| Comparative Example 2 | OTPM-RuPC | $C_{88}H_{65}N_8RuS_8$ | 1592.11 | 1592 | Calcd.: | C, 66.39; H, 4.12; N, 7.04; S, 16.11 |
| | | | | | Found: | C, 66.37; H, 4.12; N, 7.00; S, 16.11 |
| Example 1 | $PbPC_{3:1}$ | $C_{79}H_{66}N_8O_3PPbS_6$ | 1605.99 | 1606 | Calcd.: | C, 59.08; H, 4.14; N, 6.98; S, 11.98; O, 2.99 |
| | | | | | Found: | C, 59.13; H, 4.15; N, 6.98; S, 11.20; O, 3.05 |
| Example 2 | $PbPC_{3:1}$—OH | $C_{75}H_{58}N_8O_3PPbS_6$ | 1549.88 | 1550 | Calcd.: | C, 64.06; H, 4.16; N, 7.97; S, 13.68; O, 3.10 |
| | | | | | Found: | C, 64.13; H, 4.19; N, 7.80; S, 13.56; O, 3.10 |
| Example 3 | $RuPC_{3:1}$ | $C_{79}H_{66}N_8O_3PRuS_6$ | 1499.86 | 1500 | Calcd.: | C, 63.26; H, 4.44; N, 7.47; S, 12.83; O, 3.20 |
| | | | | | Found: | C, 63.25; H, 4.45; N, 7.42; S, 12.86; O, 3.15 |
| Example 4 | $RuPC_{3:1}$—OH | $C_{75}H_{58}N_8O_3PRuS_6$ | 1443.75 | 1443 | Calcd.: | C, 62.39; H, 4.05; N, 7.76; S, 13.33; O, 3.32 |
| | | | | | Found: | C, 62.42; H, 4.01; N, 73.81; S, 13.33; O, 3.35 |
| Example 5 | $PbPC_{2:2}$ | $C_{70}H_{67}N_8O_6P_2PbS_4$ | 1513.74 | 1514 | Calcd.: | C, 55.54; H, 4.46; N, 7.40; S, 8.47; O, 6.34 |
| | | | | | Found: | C, 5.54; H, 4.45; N, 7.36; S, 8.46; O, 6.39 |
| Example 6 | $PbPC_{2:2}$—OH | $C_{62}H_{51}N_8O_6P_2PbS_4$ | 1401.53 | 1401 | Calcd.: | C, 53.13; H, 3.67; N, 8.00; S, 9.15; O, 6.85 |
| | | | | | Found: | C, 53.13; H, 3.65; N, 7.91; S, 9.15; O, 6.89 |
| Example 7 | $RuPC_{2:2}$ | $C_{70}H_{67}N_8O_6P_2RuS_4$ | 1407.61 | 1407 | Calcd.: | C, 59.73; H, 4.80; N, 7.96; S, 9.11; O, 6.82 |
| | | | | | Found: | C, 59.70; H, 4.83; N, 7.94; S, 9.21; O, 6.85 |
| Example 8 | $RuPC_{2:2}$—OH | $C_{62}H_{51}N_8O_6P_2RuS_4$ | 1295.4 | 1295 | Calcd.: | C, 57.49; H, 3.97; N, 8.65; S, 9.90; O, 7.41 |
| | | | | | Found: | C, 57.44; H, 3.98; N, 8.65; S, 9.92; O, 10.14 |
| Example 9 | $PbPC_{1:3}$ | $C_{61}H_{68}N_8O_9P_3PbS_2$ | 1421.49 | 1421 | Calcd.: | C, 51.54; H, 4.82; N, 7.88; S, 4.51; O, 10.13 |
| | | | | | Found: | C, 51.56; H, 4.93; N, 7.88; S, 4.50; O, 10.19 |
| Example 10 | $PbPC_{1:3}$—OH | $C_{49}H_{44}N_8O_9P_3PbS_2$ | 1253.18 | 1253 | Calcd.: | C, 46.96; H, 3.54; N, 8.94.; 3, 5.12; O, 11.49 |
| | | | | | Found: | C, 46.99; H, 3.59; N, 8.91; S, 5.13; O, 10.95 |
| Example 11 | $RuPC_{1:3}$ | $C_{61}H_{68}N_8O_9P_3RuS_2$ | 1315.36 | 1315 | Calcd.: | C, 55.70; H, 5.21; N, 8.52; S, 4.88; O, 10.95 |
| | | | | | Found: | C, 55.77; H, 5.20; N, 8.49; S, 4.76; O, 10.91 |
| Example 12 | $RuPC_{1:3}$—OH | $C_{49}H_{44}N_8O_9P_3RuS_2$ | 1147.05 | 1147 | Calcd.: | C, 51.31; H, 3.87; N, 9.77; S, 5.59; O, 12.55 |
| | | | | | Found: | C, 51.33; H, 3.87; N, 9.68; S, 5.60; O, 12.51 |

[Measurement of UV-VIS Spectra]

The phthalocyanine compounds obtained in Examples 2, 6, and Comparative Example 1 were subjected to measurement of UV-VIS spectra according to the following procedure. The UV-VIS spectra are shown in FIG. 1.

Each phthalocyanine compound (5 μmols) was charged into a 100 ml brown measuring flask. Next, chloroform (hereinafter abbreviated as CFO) was added so as to completely dissolve the phthalocyanine therein, followed by measurement of UV-VIS spectra by exact dilution (to a solution concentration of $5.0 \times 10^{-5}$ mol/liter) and scanning to an extent of 400 to 900 nm. The cell used for the measurement of the UV-VIS spectra was a quartz cell with which the thickness of the solution became 1 cm.

In FIG. 1, the absorption maximum wavelength appears in the longest wavelength region for OTPM-PbPC (Comparative Example 1), followed by shifting to a longer wavelength region side in the order of $PbPC_{3:1}$—OH (Example 2), $PbPC_{2:2}$—OH (Example 6) and $PbPC_{1:3}$—OH (Example 10). The results reveal that when the number of side chain units constituting the phthalocyanine skeleton is changed, the position of the absorption maximum wavelength can be controlled.

[3] Preparation of Organic Thin Films

Example 13

Using $PbPC_{3:1}$-OH obtained in Example 2, a 100 nm thick organic thin film was formed by preparing a 3.0 wt % CFO solution to spin-coat it onto a titania electrode fabricated according to the following procedure, preliminarily baking on a hot plate at 50° C. for five minutes and baking at 120° C. for five minutes.

(Fabrication of Titania Electrode)

A titania electrode was formed by coating a water-polyethylene glycol dispersion of rutile titania (solid content: 30 wt %) onto a 11 mm thick ITO glass substrate of □25×25 mm size by a spin coating method, preliminarily drying on a hot plate at 120° C. for five minutes and finally baking in an oven at 500° C. for 30 minutes thereby forming a 10 μm thick film of about 20 to 30 nm spherical anatase crystals.

Example 14

In the same manner as in Example 13 except that RuPC$_{1:3}$—OH synthesized in Example 4 as a 100 nm thick organic thin film was prepared.

Example 15

In the same manner as in Example 13 except that PbPC$_{2:2}$—OH synthesized in Example 6 was used, a 100 nm thick organic thin film was prepared.

Example 16

In the same manner as in Example 13 except that RuPC$_{2:2}$—OH synthesized in Example 8 was used, a 100 nm thick organic thin film was prepared.

Example 17

In the same manner as in Example 13 except that PbPC$_{1:3}$—OH synthesized in Example 10 was used, a 100 nm thick organic thin film was prepared.

Example 18

In the same manner as in Example 13 except that RuPC$_{1:3}$—OH synthesized in Example 12 was used, a 100 nm thick organic thin film was prepared.

Comparative Example 3

In the same manner as in Example 13 except that OTPM-PbPC synthesized in Comparative Example 1 was used, a 100 nm thick organic thin film was prepared.

Comparative Example 4

In the same manner as in Example 13 except that OTPM-RuPC synthesized in Comparative Example 2 was used, a 100 nm thick organic thin film was prepared.

(1) Adhesion Test

The organic thin films prepared in the above Examples 13 to 18 and Comparative Examples 3 and 4 were subjected to measurement of a degree of adhesion by use of SAICAS. The degree of adhesion used herein indicates an adhesion between underlying titania and an organic film.

The adhesion test was carried out by measuring by use of a blade having a blade edge of 0.3 mm, a rake angle of 40° and a relief angle of 10° under conditions a measuring interval of two seconds, a horizontal speed of 200 nm/second, a vertical speed of 2 nm/second, a shear angle of 45°, a blade edge adjusting load of 0.01 N, and an initial contact load of 0.01 N. The test results are shown in Table 2.

After the adhesion test, the portion scanned with the blade was observed by use of an optical microscope (×5), confirming that the underlying substrate was not scraped off.

It will be noted that the value of the degree of adhesion is maximum at 1, which means the best degree of adhesion. The degree of adhesion of 1 indicates that the adhesion at the interface between the underlying substrate and the organic film is perfect, meaning arrival at the underlying substrate without lowering of a horizontal force. In contrast, incomplete adhesion results in the lowering of the horizontal force. More particularly, the degree of adhesion may be defined as a ratio between the peak value of horizontal force at the cutting stage and the value of horizontal force at the time of interfacial peeling.

TABLE 2

| Entry | Abbreviation | Degree of Adhesion |
| --- | --- | --- |
| Example 13 | PbPC$_{3:1}$—OH | 0.67 |
| Example 14 | RuPC$_{3:1}$—OH | 0.70 |
| Example 15 | PbPC$_{2:2}$—OH | 0.79 |
| Example 16 | RuPC$_{2:2}$—OH | 0.80 |
| Example 17 | PbPC$_{1:3}$—OH | 0.81 |
| Example 18 | RuPC$_{1:3}$—OH | 0.85 |
| Comparative Example 3 | OTPM-PbPC | 0.55 |
| Comparative Example 4 | OTPM-RuPC | 0.56 |

As shown in Table 2, Examples 13 to 18 having a phosphate group in the molecule and Comparative Examples 3 and 4 having no phosphate group in the molecule significantly differ from each other with respect to the degree of adhesion.

More particularly, when comparing the degrees of adhesion of MtPCs whose central metal is lead, OTPM-PbPC having no P=O(OH)$_2$ (hereinafter abbreviated as a phosphonate unit) is at 0.55, and PbPC$_{3:1}$—OH substituted with one phosphonate unit is at 0.67, PbPC$_{2:2}$—OH substituted with two phosphonate units is at 0.79 and PbPC$_{1:3}$—OH substituted with three phosphonate units is at 0.81, revealing that an increasing number of phosphonate units lead to a more improved degree of adhesion to titania.

When comparing the degrees of adhesion of MtPCs whose central metal is ruthenium, OTPM-RuPC substituted with no phosphonate unit is at 0.56, and RuPC$_{3:1}$—OH substituted with one phosphonate unit is at 0.70, RuPC$_{2:2}$—OH substituted with two phosphonate units is at 0.80 and RuPC$_{1:3}$—OH substituted with three phosphonate units is at 0.85, revealing that an increasing number of phosphonate units lead to a more improved degree of adhesion to titania, like MtPCs wherein the central metal is lead.

The comparison between lead and ruthenium serving as a central metal reveals that ruthenium is better than lead with respect to the degree of adhesion.

In view of the evaluation results of the degree of adhesion, it will be seen that an increasing number of phosphonate units of the MtPC skeleton, i.e. an increasing number of hydroxyl groups, contribute to improve the degree of adhesion with titania. The degree of adhesion between the phthalocyanine film and titania can be controlled by increasing or decreasing the number.

[Measurement of Ip]

The organic thin films prepared in the above Examples 13 to 18 and Comparative Examples 3 and 4 were subjected to measurement of Ip. The results are shown in Table 3.

TABLE 3

| Entry | Abbreviation | Ip [eV] |
|---|---|---|
| Example 13 | PbPC$_{3:1}$—OH | 5.06 |
| Example 14 | RuPC$_{3:1}$—OH | 5.08 |
| Example 15 | PbPC$_{2:2}$—OH | 5.19 |
| Example 16 | RuPC$_{2:2}$—OH | 5.22 |
| Example 17 | PbPC$_{1:3}$—OH | 5.33 |
| Example 18 | RuPC$_{1:3}$—OH | 5.35 |
| Comparative Example 3 | OTPM-PbPC | 4.82 |
| Comparative Example 4 | OTPM-RuPC | 4.88 |

As shown in Table 3, it has been confirmed that a difference is made between Examples 13 to 18 having a phosphate group or groups in the molecule and Comparative Examples 3 and 4 having no phosphate group.

More particularly, when comparing Ip values of MtPCs wherein the central metal is lead, OTPM-PbPC substituted with no phosphonate unit is at 4.82 eV, and PbPC$_{3:1}$—OH substituted with one phosphonate unit is at 5.06 eV, PbPC$_{2:2}$—OH substituted with two phosphonate units is at 5.19 eV and PbPC$_{1:3}$—OH substituted with three phosphonate units is at 5.33 eV, revealing that an increasing number of phosphonates units lead to deeper Ip.

When comparing Ip values of MtPCs wherein the central metal is ruthenium, OTPM-RuPC substituted with no phosphonate unit is at 4.88 eV, and RuPC$_{3:1}$—OH substituted with one phosphonate unit is at 5.08 eV, RuPC$_{2:1}$—OH substituted with two phosphonate units is at 5.22 eV and PbPC$_{1:3}$—OH substituted with three phosphonate units is at 5.35 eV, revealing that an increasing number of phosphonate units lead to deeper Ip, like the MtPC wherein the central metal is lead.

As having stated hereinabove, it has been found that the increase in number of phosphonate units of the MtPC skeleton, i.e. the increase in number of the hydroxyl groups, results in the increase of Ip. In other words, it will be said that Ip can be controlled by increasing or decreasing the number of the substituents, making it possible to appropriately set work functions.

As illustrated above, the use of the phthalocyanine compound of the invention enables an organic thin film to be obtained as being good at adhesion with titania and having an absorption maximum wavelength that is in the vicinity of or in the near infrared region.

This organic thin film not only has high affinity for titania, but also is able to control Ip on application as at least one layer of electronic device structures and thus, has been suggested to be useful as a charge transport material.

Accordingly, it will be expected that the phthalocyanine compound of the invention having affinity for titania contributes to develop functions as organic solar cells, photoelectric conversion devices and energy storage devices.

The invention claimed is:

1. A compound, represented by the formula (1)

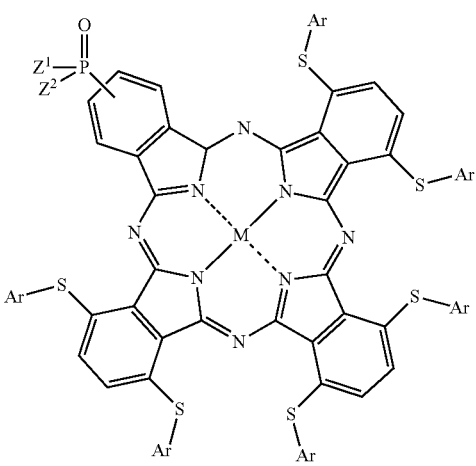

(1)

[wherein M represents a hydrogen atom, or a central metal selected from Li, Be, Na, Mg, Al, Si, K, Ca, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Ba, Hf, Ta, W, Re, Os, Ir, Pt, Au, Hg, Ti, Pb, Ce, Pr, Nd, Pm, Sm, Eu, Gd, Tb, Dy, Ho, Er, Tm, Yb, Lu, Th, Pa, U, Np and Am, $Z^1$ and $Z^2$ independently represent a hydroxyl group, an alkoxy group having 1 to 18 carbon atoms, or a phenyl group, and Ar represents at least one aryl group selected from the formulas (2) to (12)

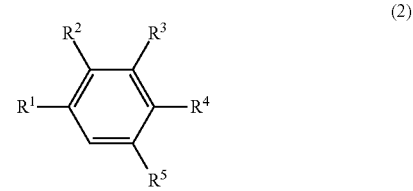

(2)

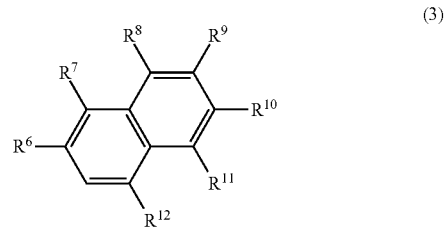

(3)

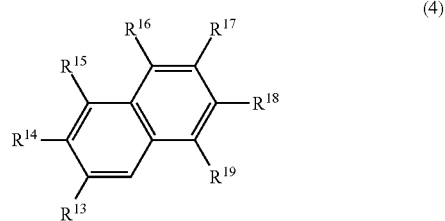

(4)

-continued

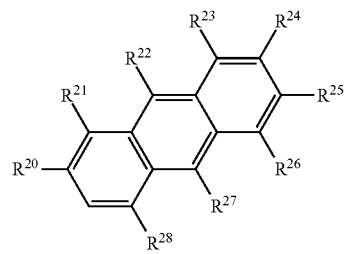
(5)

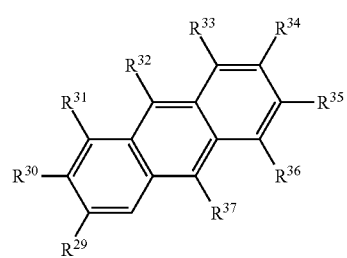
(6)

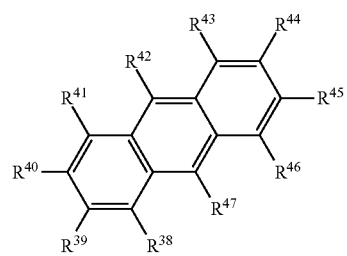
(7)

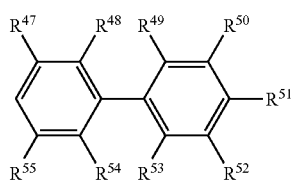
(8)

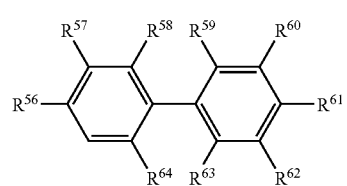
(9)

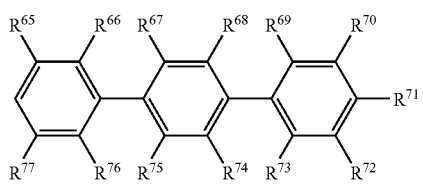
(10)

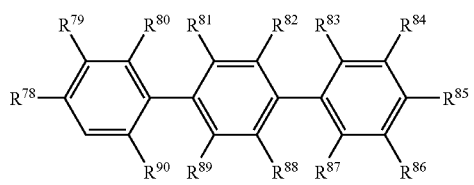
(11)

-continued

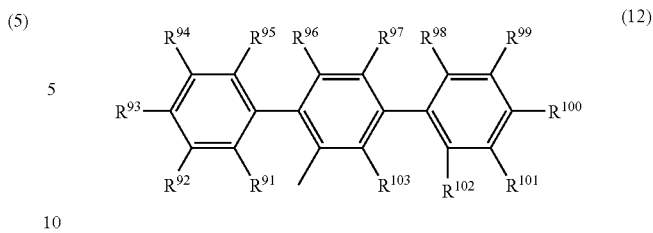
(12)

(in the formulas (2) to (12), $R^1$ to $R^{103}$ independently represent a hydrogen atom, a halogen atom, a hydroxyl group, an amino group, a silanol group, a thiol group, a carboxyl group, a phosphoric group, a phosphoric ester group, an ester group, a thioester, an amide group, a nitro group, a monovalent hydrocarbon group, an organooxy group, an organoamino group, an organosilyl group, an organothio group, an acyl group or a sulfone group)].

2. A compound, represented by the formula (13)

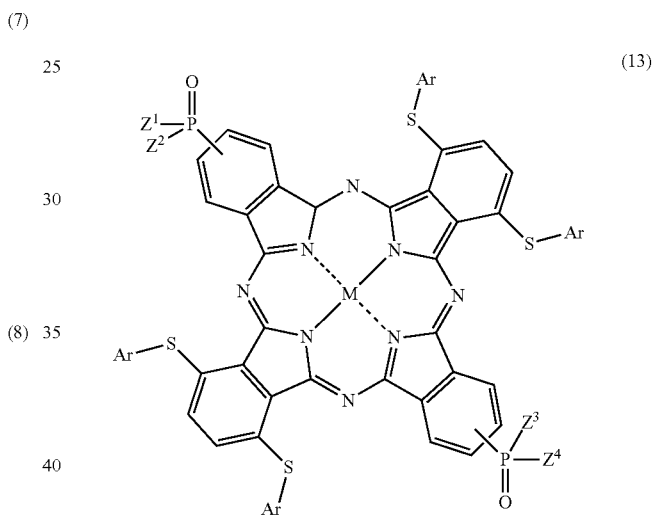
(13)

[wherein M represents a hydrogen atom, or a central metal selected from Li, Be, Na, Mg, Al, Si, K, Ca, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Ba, Hf, Ta, W, Re, Os, Ir, Pt, Au, Hg, Tl, Pb, Ce, Pr, Nd, Pm, Sm, Eu, Gd, Tb, Dy, Ho, Er, Tm, Yb, Lu, Th, Pa, U, Np and Am, $Z^1$ to $Z^4$ independently represent a hydroxyl group, an alkoxy group having 1 to 18 carbon atoms, or a phenyl group, and Ar represents at least one aryl group selected from the formulas (2) to (12)

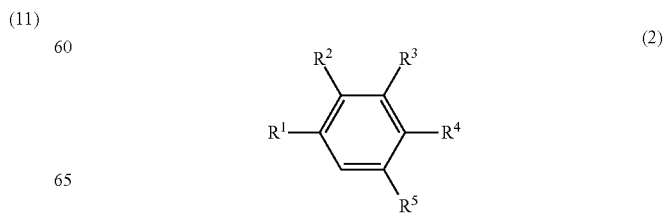
(2)

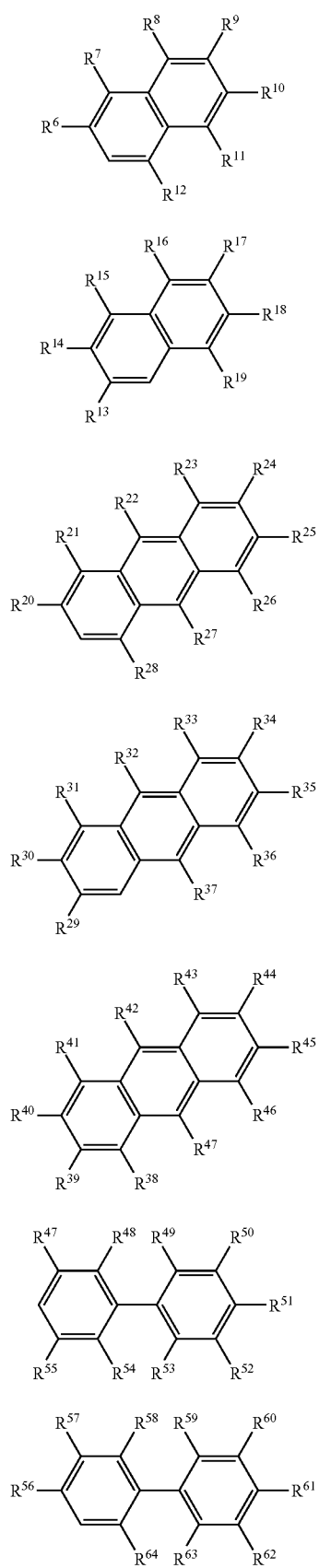

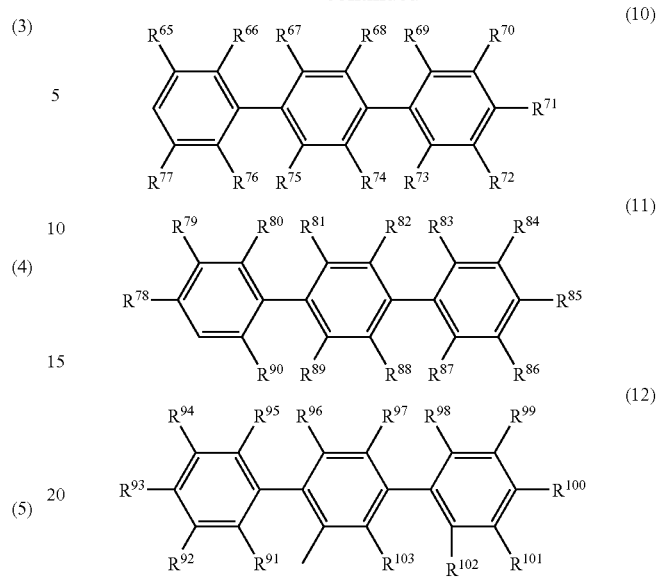

(in the formulas (2) to (12), $R^1$ to $R^{103}$ independently represent a hydrogen atom, a halogen atom, a hydroxyl group, an amino group, a silanol group, a thiol group, a carboxyl group, a phosphoric group, a phosphoric ester group, an ester group, a thioester group, an amide group, a nitro group, a monovalent hydrocarbon group, an organooxy group, an organoamino group, an organosilyl group, an organothio group, an acyl group or a sulfone group)].

3. A compound, represented by the formula (14)

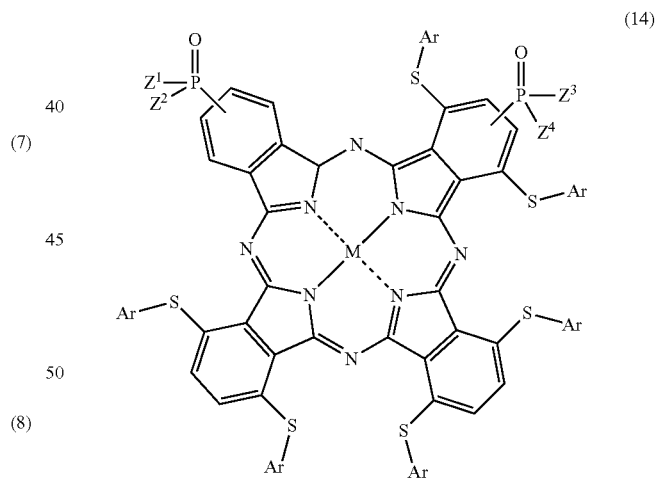

[wherein M represents a hydrogen atom, or a central metal selected from Li, Be, Na, Mg, Al, Si, K, Ca, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Ba, Hf, Ta, W, Re, Os, Ir, Pt, Au, Hg, Tl, Pb, Ce, Pr, Nd, Pm, Sm, Eu, Gd, Tb, Dy, Ho, Er, Tm, Yb, Lu, Th, Pa, U, Np and Am, $Z^1$ to $Z^4$ independently represent a hydroxyl group, an alkoxy group having 1 to 18 carbon atoms, or a phenyl group, and Ar represents at least one aryl group selected from the formulas (2) to (12)

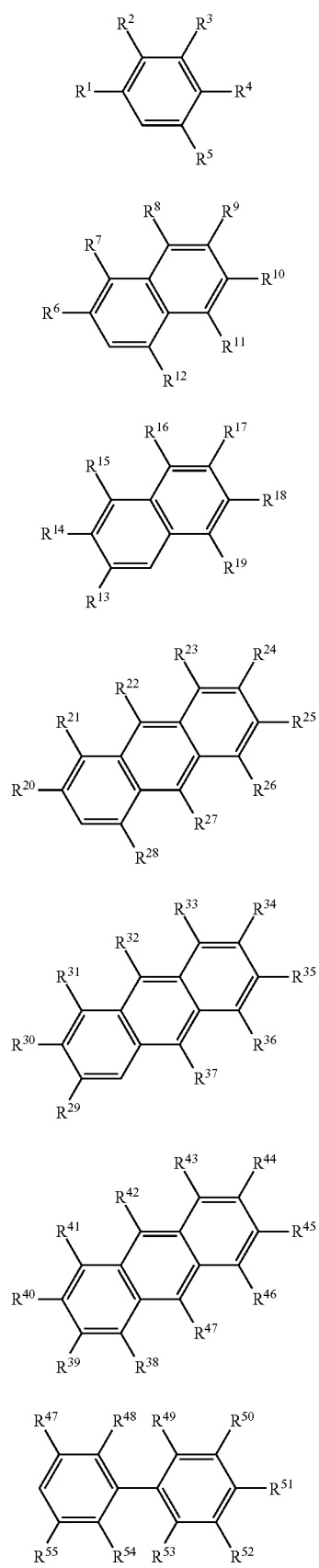

(in the formulas (2) to (12), $R^1$ to $R^{103}$ independently represent a hydrogen atom, a halogen atom, a hydroxyl group, an amino group, a silanol group, a thiol group, a carboxyl group, a phosphoric group, a phosphoric ester group, an ester group, a thioester group, an amide group, a nitro group, a monovalent hydrocarbon group, an organooxy group, an organoamino group, an organosilyl group, an organothio group, an acyl group or a sulfone group)].

4. A compound, represented by the formula (15)

[wherein M represents a hydrogen atom, or a central metal selected from Li, Be, Na, Mg, Al, Si, K, Ca, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Ba, Hf, Ta, W, Re, Os, Ir, Pt, Au, Hg, Ti, Pb, Ce, Pr, Nd, Pm, Sm, Eu, Gd, Tb, Dy, Ho, Er, Tm, Yb, Lu, Th, Pa, U, Np and Am, $Z^1$ to $Z^6$ independently represent a hydroxyl group, an alkoxy group having 1 to 18 carbon atoms, or a phenyl group, and Ar represents at least one aryl group selected from the formulas (2) to (12)

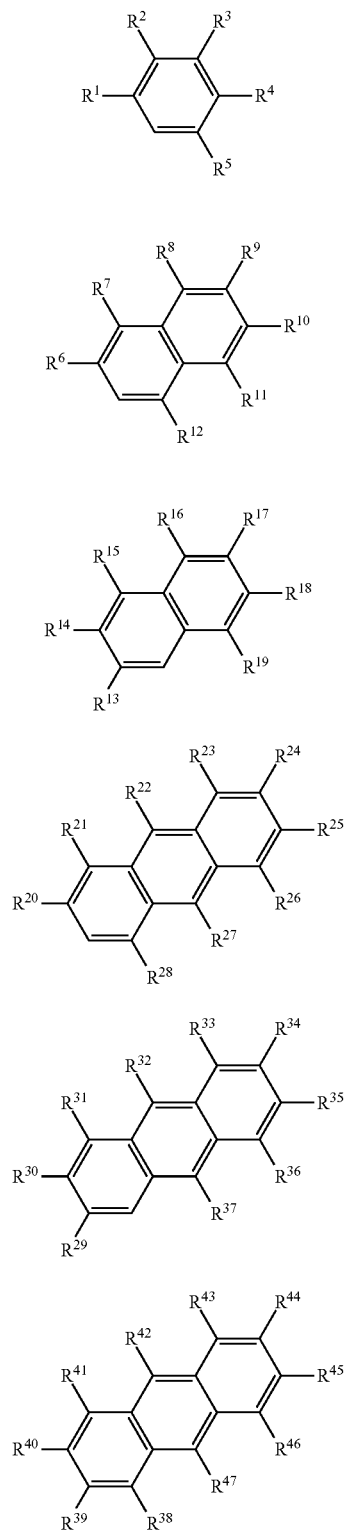

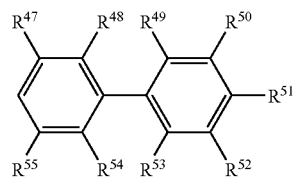

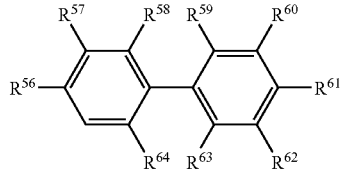

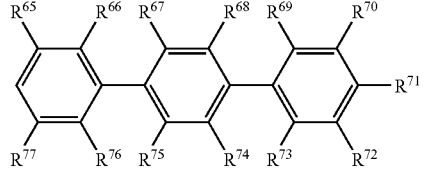

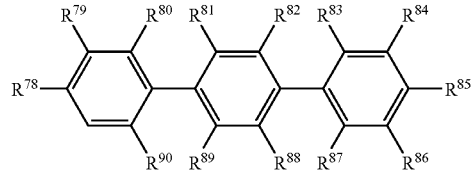

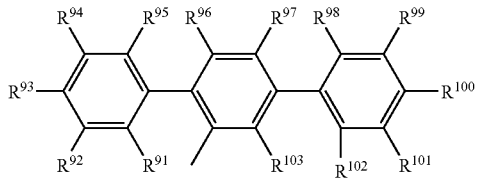

(in the formulas (2) to (12), $R^1$ to $R^{103}$ independently represent a hydrogen atom, a halogen atom, a hydroxyl group, an amino group, a silanol group, a thiol group, a carboxyl group, a phosphoric group, a phosphoric ester group, an ester group, a thioester group, an amide group, a nitro group, a monovalent hydrocarbon group, an organooxy group, an organoamino group, an organosilyl group, an organothio group, an acyl group or a sulfone group)].

5. A compound, represented by the formula (16)

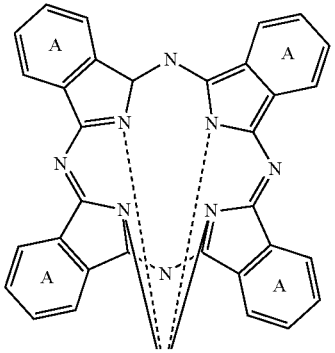

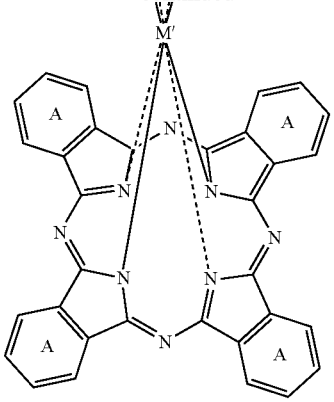

[wherein M' represents a lanthanoid or actinoid forming a double nucleus structure,

represents an aryl group represented by the formula (17) or (18) (provided that at least one is an aryl group represented by the formula (17)),

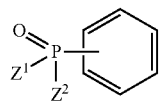
(17)

(in the formula (17), $Z^1$ and $Z^2$ independently represent a hydroxyl group, an alkoxy group having 1 to 18 carbon atoms, or a phenyl group)

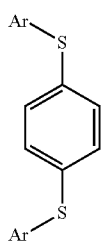
(18)

(in the formula (18), Ar represents at least one aryl group selected from the formulas (2) to (12)

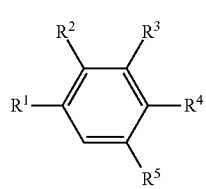
(2)

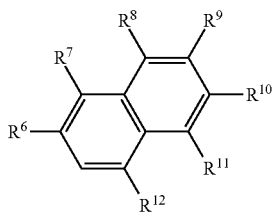
(3)

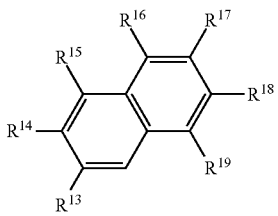
(4)

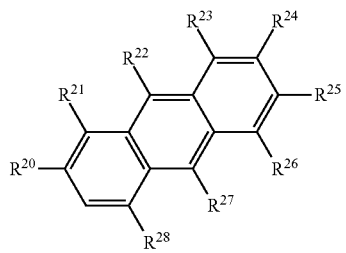
(5)

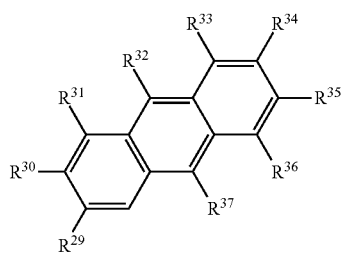
(6)

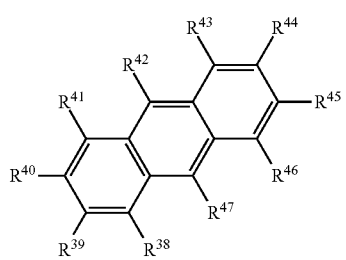
(7)

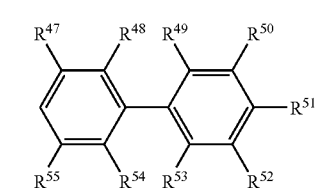
(8)

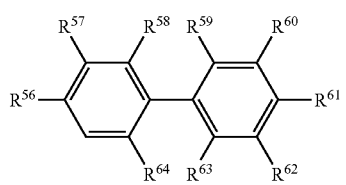
(9)

-continued

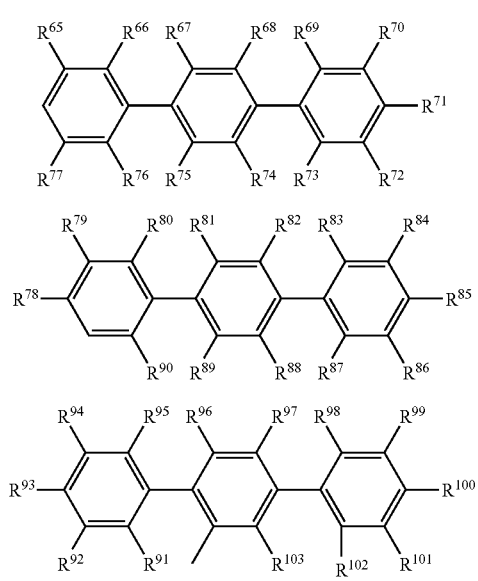

(in the formulas (2) to (12), $R^1$ to $R^{103}$ independently represent a hydrogen atom, a halogen atom, a hydroxyl group, an amino group, a silanol group, a thiol group, a carboxyl group, a phosphoric group, a phosphoric ester group, an ester group, a thioester group, an amide group, a nitro group, a monovalent hydrocarbon group, an organooxy group, an organoamino group, an organosilyl group, an organothio group, an acyl group or a sulfone group)].

6. A composition comprising the compound defined in claim 1.

7. A varnish comprising the compound defined in claim 1.

8. An organic thin film obtained from the compound defined in claim 1.

9. An organic thin film prepared from the varnish defined in claim 7.

10. An electronic device comprising at least one layer of the organic thin film defined in claim 8.

11. An organic solar cell comprising at least one layer of the organic thin film defined in claim 8.

12. A photoelectric conversion device comprising at least one layer of the organic thin film defined in claim 8.

13. An energy storage device comprising at least one layer of the organic thin film defined in claim 8.

* * * * *